US009956057B2

(12) United States Patent
Essler et al.

(10) Patent No.: US 9,956,057 B2
(45) Date of Patent: May 1, 2018

(54) METHOD FOR MANUFACTURING A CARTRIDGE FOR CONTAINING AND METERABLY DISPENSING A FLOWABLE DENTAL MATERIAL AND SUCH A CARTRIDGE

(71) Applicant: pheneo GmbH, Bremen (DE)

(72) Inventors: Michael Essler, Cuxhaven (DE); Sasan Habibi-Naini, Fischerhude (DE)

(73) Assignee: Pheneo GmbH, Bremen (DE)

( * ) Notice: Subject to any disclaimer, the term of this patent is extended or adjusted under 35 U.S.C. 154(b) by 0 days. days.

(21) Appl. No.: 14/767,463

(22) PCT Filed: Feb. 13, 2014

(86) PCT No.: PCT/EP2014/052863
§ 371 (c)(1),
(2) Date: Aug. 12, 2015

(87) PCT Pub. No.: WO2014/125051
PCT Pub. Date: Aug. 21, 2014

(65) Prior Publication Data
US 2015/0374459 A1    Dec. 31, 2015

(30) Foreign Application Priority Data

Feb. 15, 2013 (DE) .................. 10 2013 002 604
Mar. 11, 2013 (DE) .................. 10 2013 004 077

(51) Int. Cl.
*A61C 5/06* (2006.01)
*B29C 45/16* (2006.01)
(Continued)

(52) U.S. Cl.
CPC .............. *A61C 5/062* (2013.01); *A61C 5/62* (2017.02); *A61C 5/66* (2017.02); *B29C 45/16* (2013.01);
(Continued)

(58) Field of Classification Search
CPC .. A61C 5/062; A61C 5/66; A61C 5/62; A61C 3/005; B29C 45/16; B29C 45/1676; B29L 2031/7544
See application file for complete search history.

(56) References Cited

U.S. PATENT DOCUMENTS 3,739,947 A    6/1973  Baumann et al.
4,184,490 A    1/1980  Jacklich
(Continued)

FOREIGN PATENT DOCUMENTS

DE        199 34 235 A1    10/2000
DE    10 2008 057443 A1     5/2010
(Continued)

*Primary Examiner* — Ryan J Walters
(74) *Attorney, Agent, or Firm* — McGlew and Tuttle, P.C.

(57) ABSTRACT

A method is for manufacturing a cartridge (10, 27, 30) for containing and meterably dispensing a reservoir (11) contained flowable dental material (36). The reservoir (11) is connected to a cannula section (14) for dispensing the dental material (36). A separate functional element (15) is connected to the cannula section (14). The cartridge (10, 27, 30) is manufactured together with the functional element (15) according to a multicomponent injection molding method. The functional element (15) is designed as a detachable closing element. The functional element (15) and the cartridge (10, 27, 30) are positioned during the manufacture such that the functional element (15) is mounted at least partially in the cannula section (14). The functional element (15) has a plug part (16) for closing the cannula section (14) and a cannula duct (24) of the cannula section (14) is filled at least partially with the plug part (16).

20 Claims, 15 Drawing Sheets

(51) Int. Cl.
*A61C 5/62* (2017.01)
*A61C 5/66* (2017.01)
*B29L 31/00* (2006.01)
*A61C 3/00* (2006.01)

(52) U.S. Cl.
CPC ......... *B29C 45/1676* (2013.01); *A61C 3/005* (2013.01); *B29L 2031/7544* (2013.01)

(56) References Cited

U.S. PATENT DOCUMENTS

| | | | |
|---|---|---|---|
| 4,391,590 A | | 7/1983 | Dougherty |
| 5,129,825 A | | 7/1992 | Discko, Jr. |
| 6,059,570 A | | 5/2000 | Dragan et al. |
| 6,422,866 B2 | * | 7/2002 | Dragan .................. 215/252 |
| 2001/0009754 A1 | * | 7/2001 | Dragan .................. A61O 5/62 433/89 |
| 2011/0027753 A1 | * | 2/2011 | Maurat .................. A61O 5/062 433/141 |
| 2011/0151403 A1 | * | 6/2011 | Pauser .................. A61O 5/62 433/82 |
| 2011/0289707 A1 | * | 12/2011 | Schaefer ............ A46B 15/0002 15/105 |

FOREIGN PATENT DOCUMENTS

| | | |
|---|---|---|
| DE | 10 2009 017 980 A1 | 11/2010 |
| EP | 0 141 083 A1 | 5/1985 |
| EP | 2 133 038 A1 | 12/2009 |
| EP | 2329791 A2 | 6/2011 |
| EP | 2 497 440 A1 | 9/2012 |
| WO | 02/36033 A1 | 5/2002 |

* cited by examiner

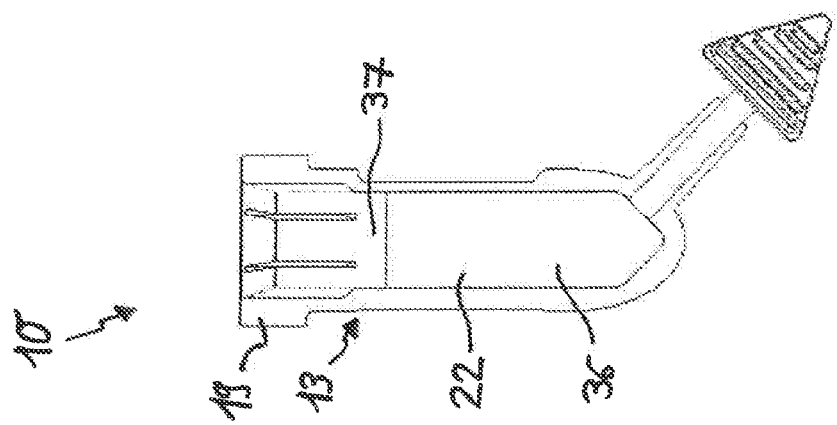
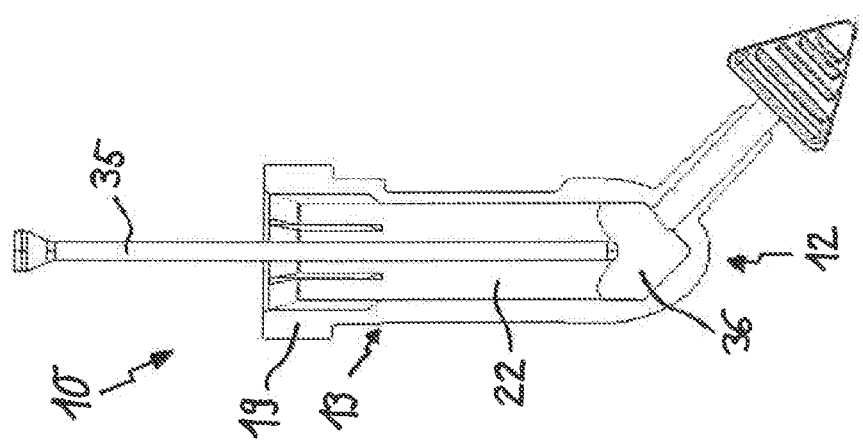
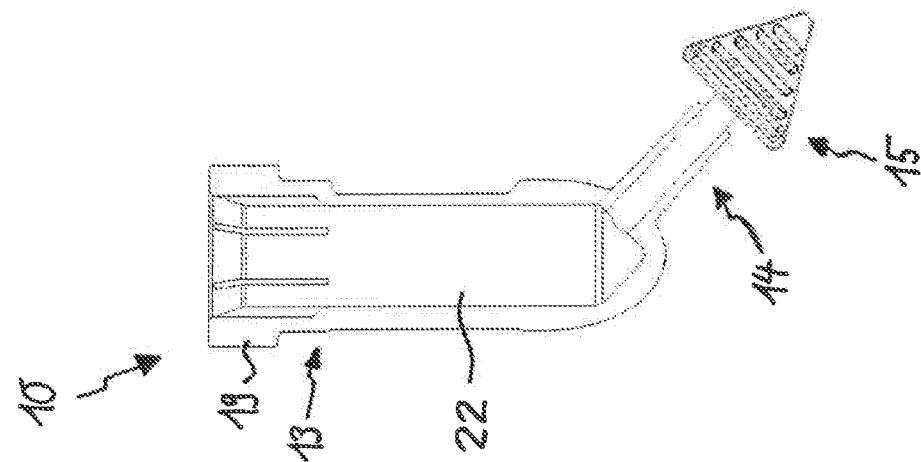

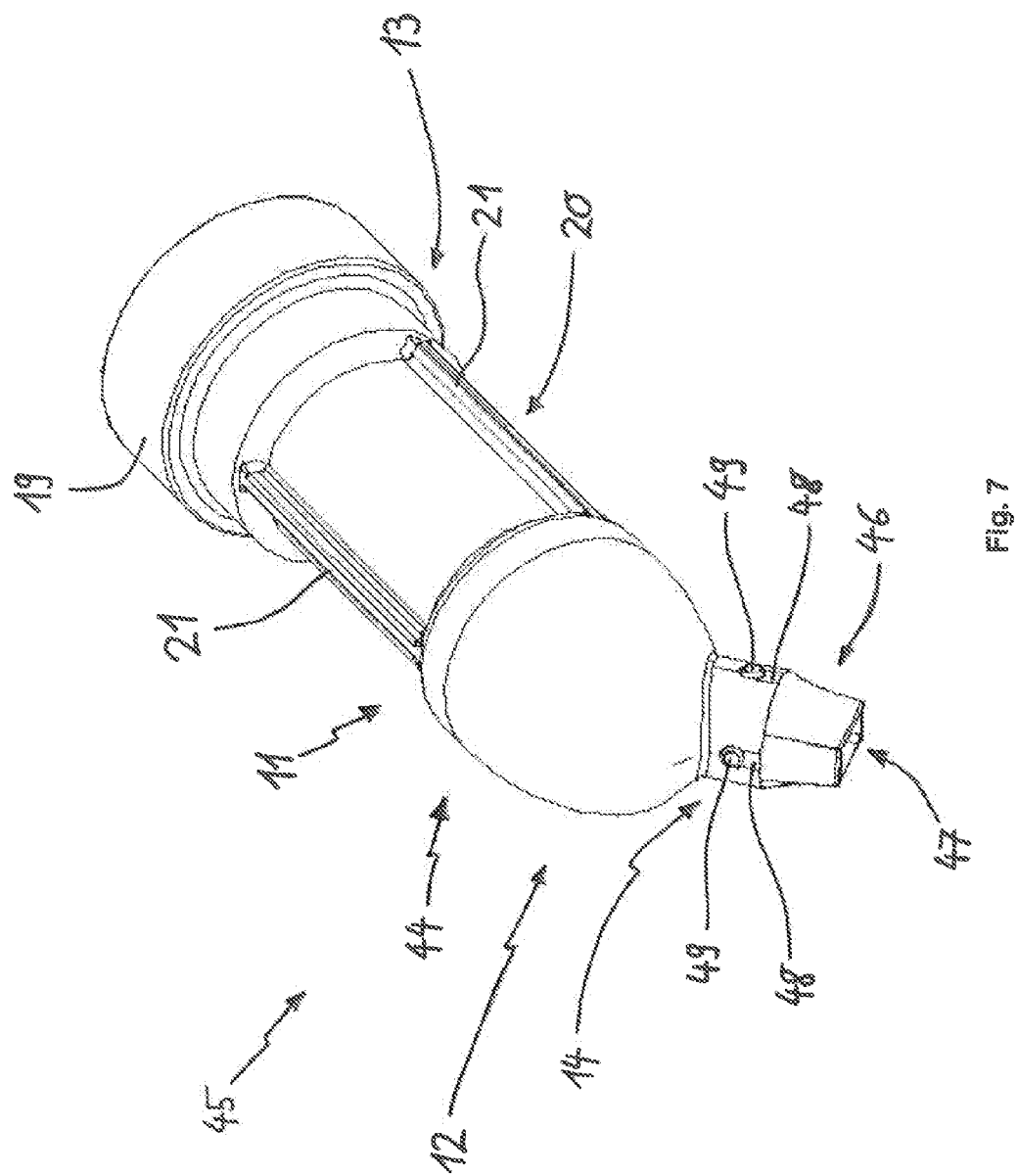

METHOD FOR MANUFACTURING A CARTRIDGE FOR CONTAINING AND METERABLY DISPENSING A FLOWABLE DENTAL MATERIAL AND SUCH A CARTRIDGE

CROSS REFERENCE TO RELATED APPLICATIONS

This application is a United States National Phase Application of International Application PCT/EP2014/052863 filed Feb. 13, 2014 and claims the benefit of priority under 35 U.S.C. § 119 of German Patent Applications 10 2013 002 604.0 filed Feb. 15, 2013 and 10 2013 004 077.9 filed Mar. 11, 2013 the entire contents of which are incorporated herein by reference.

FIELD OF THE INVENTION

The present invention pertains to a method for manufacturing a cartridge for containing and meterably dispensing a flowable dental material with a reservoir for containing the dental material, wherein the reservoir is connected to a cannula section for dispensing the dental material from the reservoir, and with a separate functional element, which is connected to the cannula section, wherein the cartridge is manufactured together with the functional element according to a multicomponent injection molding method. Furthermore, the present invention pertains to a cartridge, which is manufactured according to the method according to the present invention, for containing and meterably dispensing a flowable dental material with a reservoir for containing the dental material, wherein the reservoir is connected to the cannula section for dispensing the dental material from the reservoir, and with a separate functional element, which is associated with the cannula section, wherein the cartridge and the functional element are designed as a common multicomponent injection-molded part.

BACKGROUND OF THE INVENTION

Such a cartridge is known from DE 10 2008 057 443 A1, where the functional element is a valve device.

It is known from U.S. Pat. No. 4,391,590 B1 that a functional element is designed as a cap, which is pulled over a cannula opening of a cannula duct to close the cannula section. It is disadvantageous here that the cartridge and the cap for the cartridge must be manufactured in two mutually independent manufacturing steps, wherein the cap is placed, as a rule, by hand by a person or in an automated manner on the cannula opening of the cannula section. This causes high manufacturing costs. In addition, with the cap already placed, there is a risk of air inclusions during the filling of the cartridge with the dental material, as result of which the shelf life of the dental material may be reduced and/or the quantity of the filling may show undesired variations in a comparison of a plurality of cartridges. Such air inclusions may lead to the loss of the cap, especially during transportation, because of the expansion of the air, as a result of which the storage stability is reduced. Even though the inclusion of air can be reduced when filling the cartridge without cap, there is a risk now that dental material will escape from the cannula opening of the cannula section, as a result of which dental material will be lost. This leads to higher manufacturing costs. Such cartridges are intended for single-time use especially in the field of dentistry. However, there is a risk when using caps that the cannula section will be reclosed with the cap in order to use a residual material that is preset later. There is a risk of contamination of the dental material and/or of an increased risk for infection because of its undesired reclosing of the cartridge that was once opened.

A cartridge, in which fibers or a flocking are connected to the cartridge in the area of an outlet of the cannula section, is known from U.S. Pat. No. 6,059,570. This functional element is used to apply, spread and/or burnish the dental material. It is disadvantageous here that the application of the fibers or of the flocking is carried out in an independent manufacturing step and fully independently from the manufacture of the cartridge. It is also disadvantageous that the cannula section is rigid in the area of the fibers or flocking. As a result, there is a risk that a treatment with the functional element is perceived by a patient as being unpleasant and/or painful. In addition, there is a risk that undesired injuries will develop because of the rigid design. The spreading and/or burnishing of the dental material is also made difficult by the rigid design of the cartridge and of the cannula section.

Furthermore, it is disadvantageous in prior-art cartridges that there is a risk of an especially abrupt rupture of material in case of an overstressing due to an excessively strong force or an excessively high pressure being applied to press the dental material out of the cartridge and/or the reservoir.

SUMMARY OF THE INVENTION

A basic object of the present invention is to perfect a method and a cartridge of the type mentioned in the introduction such that the manufacturing process and the cartridge can be manufactured in a more cost-effective manner, a possibly air-free filling of the cartridge is made possible, and/or reclosing of the cartridges after they had been opened for the first time is prevented to the extent possible. Another basic object of the present invention is preferably to perfect a method and a cartridge of the type mentioned in the introduction such that an especially abrupt rupture of material is prevented and/or the risk of a rupture of material can be recognized in time.

The basic object of the present invention is accomplished with a method of the type mentioned in the introduction, in which the functional element is designed as a detachable closing element, wherein the functional element and the cartridge are positioned in relation to one another already during the manufacture such that the functional element is mounted at least partially in the cannula section, and the functional element has a plug part for closing the cannula section, and a cannula duct of the cannula section is filled at least partially with the plug part. Furthermore, the cartridge mentioned in the introduction is characterized, for accomplishing the object, in that the functional element is designed as a closing element for closing a cannula duct of the cannula section, wherein the closing element has a detachable plug part, which is held in the cannula duct detachably, in a positive-locking and/or non-positive manner and fills the cannula duct at least partially for closing the cartridge.

The basic object of the present invention is preferably accomplished with a method of the type mentioned in the introduction, in which the cartridge is manufactured with a wall thickness reduced in the middle area of the reservoir. Furthermore, the cartridge mentioned in the introduction may be characterized, for accomplishing the object, such that the wall thickness of the cartridge is reduced in a middle area of the reservoir.

It is advantageous in this connection that the middle area with the reduced wall thickness will first expand and/or stretch when a force and/or a pressure that is higher than a preset force or a preset working pressure is applied. As a result, the cartridge can absorb stronger forces and/or higher pressures than intended, and the risk of an abrupt rupture of material and/or of bursting of the cartridge is considerably reduced. In particular, an overstressing of the cartridge, for example, because of an excessively strong force applied to the cartridge, is easily recognizable for a user from the expansion and/or stretching of the middle area. As a result, the user can reduce the forced applied in time before the onset of a rupture of material, as a result of which a rupture of material can be avoided.

In particular, the cartridge can absorb forces of up to at least 400 N, especially up to at least 450 N, and preferably up to at least 500 N for pressing out the dental material without rupture of the material. A preset maximum working force of 300 N is provided for dispensing or pressing the dental material out of the cartridge. In particular, a usual working force for pressing the dental material out of the cartridge is in the range of 100 N to 200 N.

According to a variant, the middle area of the reservoir with the reduced wall thickness is cylindrical or at least essentially cylindrical. In particular, the middle area with the reduced wall thickness has a ring-shaped design. Furthermore, the middle area of the reservoir may extend from a first end of the cartridge with a cannula section and/or from an end face area up a second end of the cartridge with a cartridge base. In particular, the outer circumference tapers and/or the wall thickness of the cartridge decreases in the middle area in relation to the first end and the second end of the cartridge. The middle area of the reservoir is preferably expanded in the longitudinal direction in case of a force stronger than a preset working force for dispensing the dental material from the reservoir. A cartridge, which embodies the principle of the reduced-shaft bolt, is provided in the field of dentistry. In particular, the middle area of the reservoir and/or the cartridge is elastically expansible. The cartridge and/or the middle area can expand and/or be deformed by up to 2 mm, especially up to 4 mm, and preferably up to 6 mm at a force in the range of up to 100 N and/or up to 200 N applied to press the dental material out of the cartridge. At a force of up to 400 N or up to 500 N, the cartridge and/or the middle area may expand and/or be deformed by up to 8 mm, especially up to 10 mm, and preferably up to 12 mm.

According to another embodiment, which is also conceivable independently from the invention being claimed here, a functional element, which is a separate element concerning its function and is connected to the cannula section, is provided, wherein the cartridge is preferably manufactured together with the functional element according to a multicomponent injection molding method.

It is advantageous here that the functional element is manufactured together with the cartridge in a manufacturing process that is especially an automated process. The cartridge and the functional element are thus manufactured as a common multicomponent injection-molded part. A method and a cartridge are thus provided, so that the manufacturing process and the cartridge can be manufactured in a more cost-effective manner. In particular, the cartridge is manufactured together with the functional element, wherein the functional element and the cartridge are positioned in relation to one another already during the manufacture such that the functional element is mounted at least partially in the cannula section and/or on the cannula section. As a result, mounting of the functional element on and/or in the cartridge, which follows the manufacture of the functional element and of the cartridge, is thus eliminated. A cost-intensive additional manufacturing step can thus be eliminated. A separate manufacture of the cartridge and the functional element and an especially manual assembly are eliminated. Instead, the cartridge also comprises the functional element already during the manufacture by means of the multicomponent injection molding method. The cartridge with the functional element is thus designed as a multicomponent injection-molded part. A cost-effective manufacturing process or a more cost-effective cartridge can be attained hereby.

A separate functional element is defined within the framework of the present invention as a functional element that has an additional function in relation to the cartridge and/or the cartridge housing. In particular, the separate functional element is used to detachably close the cannula section and/or to apply, distribute, introduce and/or burnish the dental material. A separate functional element is preferably defined optionally within the framework of the present application as a closing element detachably connected to the cartridge or as an application element rigidly connected to the cartridge. In particular, a functional element rigidly connected to the cartridge is nondetachably connected to the cartridge and/or cannot be separated from the cartridge without destruction. A separate functional element is preferably designed as such a functional element that consists of a material different from that of the other components of the cartridge. In particular, the cartridge and/or the cartridge housing consists of a first material. The functional element preferably consists of another, especially second material different from the first material.

A complicated, especially manual closure of the cannula opening or of the cannula duct of the cannula section during the manufacture of the cartridge can be avoided, in particular, because of the multicomponent injection molding method or the multicomponent injection-molded part, especially if the functional element is designed as a closing element. The shrinkages of the materials of the cartridge housing and of the functional element, especially in case of manufacturing according to the multicomponent injection molding method, are preferably coordinated such that the functional element is detachable from the cannula section of the cartridge. As an alternative, the functional element is connected to the cartridge rigidly, especially nondetachably.

A flowable and/or viscous dental material is preferably defined within the framework of the present invention as a material used in dentistry. In particular, a cartridge according to the present invention is used in the field of dentistry, and such a cartridge may also be called a compule, capsule and/or unit dose. The cartridge and/or the reservoir is designed for containing a dental material in a quantity in the range of 0.1 g to 0.5 g and especially 0.25 g. The volume of dental material that can be contained in the cartridge and/or the reservoir may be at least 100 mm3 or 200 mm3. As an alternative to the containing and meterable dispensing of a flowable dental material, the cartridge may also be used to contain and meterably dispense any desired viscous material, especially a viscous medical substance.

According to a variant of the method according to the present invention, the multicomponent injection molding method is designed as a two-component injection molding method. The functional element can be manufactured in a first step of the two-component injection molding method from a plastic material, especially a first plastic material. The cartridge and/or a cartridge housing can be manufactured in a subsequent, second step from a second plastic material, which is especially different from the first plastic material.

In particular, a cartridge and/or a cartridge housing, which cartridge or cartridge housing has a reservoir for containing the dental material, a cannula section and/or the cartridge base, is manufactured in the second step. The cartridge and/or the cartridge housing can be manufactured and/or molded at least partially around the functional element in the second step of the two-component injection molding method. Furthermore, the cartridge and/or the cartridge housing can be molded onto the functional element in the second step. The functional element manufactured in the first step is used, in particular, at least partially as a core part, around which the cartridge and/or the cartridge housing are manufactured and completed in the second step.

As an alternative, the cartridge and/or the cartridge housing may be manufactured first in a first step of the two-component injection molding method and the functional element in a subsequent, second step. The functional element preferably consists of a thermoplastic elastomer, thermoplastic silicone, thermoplastic polyurethane, liquid silicone or polyolefin. The cartridge and/or the cartridge housing may consist of polyester, especially of polybutylene terephthalate or polyethylene terephthalate, polyolefin, especially polypropylene, polyoxymethylene, polyamide, cyclo-olefin copolymers, cyclo-olefin copolymer mixtures, polycarbonate, acrylonitrile-butadiene-styrene or styrene polymer.

The functional element and the cartridge are formed especially from different materials, preferably to avoid a connection in substance. In particular, the shrinkage of the material of the cartridge and/or of the cartridge housing is lower than the shrinkage of the material of the functional element in order to avoid a shrink fit of the functional element in the cannula section and/or the cannula duct.

According to another embodiment, a cannula duct of the cannula section is filled at least partially with the functional element. In particular, the cannula duct is filled completely by means of the functional element. Inclusion of air in the cannula duct during the filling of the cartridge with the dental material is thus avoided. The reservoir itself is used, instead, exclusively to contain the dental material. This facilitates an at least extensively air-free filling of the cartridge. In case of a functional element that extensively or completely fills the cannula duct, a contact surface between the functional element and the inner surface of the cannula duct is provided, which is large enough to hold the functional element in the cannula duct. The functional element is preferably connected to the cannula section detachably, in a positive-locking and/or non-positive manner, especially in a frictionally engaged manner. In particular, the functional element is arranged and/or held in the cannula duct detachably, in a positive-locking and/or non-positive, preferably fictionally engaged manner. Even though the functional element as a component of the cartridge is manufactured as a multicomponent injection-molded part, the functional element is not preferably made in one piece with the cartridge. The functional element may rather be designed as a component detachable from the cartridge. Such a functional element thus makes it possible to fill the cartridge possibly air-free to the extent possible and/or it can prevent reclosing of the cartridge after it had been opened for the first time. In particular, trailing flow of the material can be avoided, especially in case of low-viscosity materials, preferably so-called flowables.

According to a variant of the method, which is also conceivable independently and separately from the present invention, the functional element is designed as a detachable closing element, which has a plug part for closing the cannula section, and a cannula duct of the cannula section is filled with the plug part at least partially, especially completely. The cannula duct may have an internal diameter in the range of 0.5 mm to 2.5 mm, especially an internal diameter of 0.5 mm, 1.4 mm or 2.2 mm. The cannula section and/or the cannula duct may have a length in the range of 2 mm to 20 mm, especially at least 5 mm. The length of the cannula section and/or of the cannula duct has a slope at an angle in the range of 40° to 60° in relation to the longitudinal axis of the cartridge and/or of the reservoir. The plug part preferably has a cylindrical shape. In particular, the external diameter of the plug part corresponds to the internal diameter of the cannula duct. The functional element is preferably connected detachably to the cartridge or the cannula duct exclusively by means of the plug part arranged within the cannula duct. Additional connection surfaces, especially surfaces of the functional element surrounding the cannula duct and/or the cannula section, can thus be avoided.

The closing element preferably has a grip part, which is connected to the plug part and is especially designed as an information carrier, outside the cannula section and/or the cannula duct. The functional element and the plug part can be detached from the cartridge by means of the cartridge in a simple manner. The grip part may have any desired shape, as long as it can be grasped by a person with one hand and/or can be grasped at least between the thumb and the index finger of one hand Based on the design of the grip part, especially concerning the shape and/or color, the grip part may the used, moreover, as an information carrier for the dental material contained in the cartridge and/or the intended use. As an alternative or in addition, a logo, a QR code and/or a lot number or batch number may be printed on the grip part.

According to a variant of the method, which is also conceivable independently and separately from the present invention, the functional element is designed as an application element for dispensing and/or applying the dental material. The application element of the cartridge is thus used to release, apply, introduce and/or burnish the dental material during the treatment of a patient. The application element is connected rigidly, especially nondetachably to the cartridge and/or the cartridge housing. For example, the application element may be welded to the cartridge and/or the cartridge housing. The connection of the application element to the cartridge and/or the cartridge housing is preferably a positive-locking and/or non-positive connection. The connection may be embodied by means of adhesion based on a suitable combination of materials. In particular, the application element is shrunk at least partially onto the cartridge, the cartridge housing and/or the cannula section. The application element preferably cannot be detached from the cartridge and/or the cartridge housing without destruction. Such a functional element improves the dispensing, application and/or burnishing of the dental material.

According to another embodiment, the application element is manufactured from an elastic plastic material. Based on a soft and/or elastic plastic material for the application element, the application and/or burnishing of the dental material can, on the one hand, be performed more easily by the person carrying out the treatment, and, on the other hand, it is more pleasant and/or more gentle for the patient. In particular, the elastic plastic material of the application element has a hardness in the range of Shore-A or Shore-D, especially in the range of 30 Shore A to 90 Shore A. The material of the application element is preferably different from the material of the other components of the cartridge and/or the cartridge housing. In particular, the cartridge and/or the cartridge housing consists of a first material and the application element of a second material different from the first material.

An outlet of the application element is preferably closed with a separate and/or detachable closing element. In particular, the separate closing element is manufactured independently from the cartridge with the functional element in a separate manufacturing process. The closing element is preferably designed as a closing cap, which is pulled at least partially over the application element to close the outlet. Caps commonly used for cartridges in the field of dentistry can thus be used to close the cartridge.

According to a variant, the dental material is filled into the reservoir, especially in an automated manner, through an opening facing away from the cannula section after manufacturing the cartridge with the functional element, which preferably closes the cannula section and especially fills out the cannula duct. A plunger is preferably inserted, especially in an automated manner, into the opening to close the reservoir after filling the reservoir. The manufacture of the cartridge with the functional element, which is mounted especially to close the cannula duct, the filling of the cartridge and the insertion of a plunger to close the cartridge can thus be carried out in a fully automated manner. An intermediate step for mounting the functional element on the cartridge, especially manually, can thus be avoided, and the cartridge can be manufactured, on the whole, in a more cost-effective manner.

According to a variant of the cartridge according to the present invention, the wall thickness of the cartridge is increased in an end face area facing the cannula section. In particular, the cartridge is designed in the end face area for a pressure load of at least 2 bar, preferably at least 20 bar, and especially preferably about 31 bar. In particular, the cartridge is designed, preferably in the end face area, for a pressure load in the range of 20 bar to 320 bar, preferably in the range of 20 bar to 160 bar, and especially preferably in the range of 20 bar to 90 bar. The end face area is subject to strong forces during the pressing of the dental material out of the cartridge. Based on a reinforced end face area with a greater wall thickness relative to other areas of the cartridge, the risk of damage and/or bursting of the cartridge in the end face area is considerably reduced. The wall thickness of the cartridge is preferably reduced in a middle area of the reservoir. Considerably weaker forces occur in the middle area of the reservoir compared to other areas even during the pressing out of the dental material. It is possible as a result to reduce the wall thickness in the middle area, as a result of which material can be saved when manufacturing the cartridge and a cartridge can thus be manufactured in a more cost-effective manner. Reinforcing struts extending in the longitudinal direction of the reservoir are preferably provided in the middle area with the reduced wall thickness. As a result, the wall thickness can be reduced even more in the middle area, on the one hand, and it is guaranteed, on the other hand, by the reinforcing struts that the forces, which occur especially during the pressing out of the dental material, can be absorbed and/or transmitted without the risk of damage to or bursting of the cartridge. At least two, three, four or more reinforcing struts may be provided, which are distributed uniformly over the circumference. In particular, a total of two reinforcing struts are formed in the middle area on sides of the cartridge that are located facing away from one another.

The middle area of the reservoir is preferably designed to at least partially compensate, absorb and/or display an overstressing of the cartridge at a force and/or a pressure greater than a preset force and/or a preset working pressure for dispensing the dental material from the reservoir by expansion in the longitudinal direction of the cartridge. In particular, the middle area of the cartridge and/or of the reservoir is elastically expansible.

The wall thickness in the middle area of the reservoir and/or of the cartridge is in the range of 0.4 mm to 1 mm, especially in the range of 0.4 mm to 0.8 mm, and especially preferably 0.6 mm. Outside the middle area with the reduced wall thickness, the normal wall thickness is, especially in the area of the first and/or second end of the cartridge, in the range of 0.8 mm to 2 mm, especially in the range of 0.8 mm to 1.4 mm, and especially preferably 1.1 mm. The wall thickness in the area of the reservoir and/or of the cartridge is preferably smaller by at least ¼, especially by at least ⅓, and especially preferably by at least about ½ than the wall thickness outside the middle area with the reduced wall thickness, especially in the area of the first and/or second end of the cartridge.

In the unstressed state, the entire cartridge, especially including a cannula section, may have a maximum length in the range of 8 mm to 15 mm, especially in the range of 10 mm to 12 mm, and especially preferably about 11 mm. The middle area of the cartridge with the reduced wall thickness may have a length in the range of 2 mm to 6 mm, especially in the range of 3 mm to 4 mm, and especially preferably 3.5 mm in the unstressed state. The external diameter of the cartridge may be in the range of 2 mm to 5 mm. The external diameter of the cartridge in the middle area with the reduced wall thickness may be in the range of 2 mm to 4 mm, and especially 3 mm.

According to an embodiment, which is also conceivable independently from the invention being claimed here, a functional element is provided, which is a separate element concerning its function and is associated with the cannula section, wherein the cartridge is preferably designed together with the functional element as a multicomponent injection-molded part, especially as a two-component injection-molded part.

According to another embodiment, a cartridge base is provided for containing the cartridge in a dispensing device at an end of the reservoir facing away from the cannula section, wherein the cartridge base has an opening for accommodating a movable plunger for closing the reservoir and for pressing the dental material out of the reservoir. In particular, the cartridge base has a ring-shaped design and/or is used to receive and hold the cartridge in a dispensing device. The dispensing device is preferably used for the meterable dispensing or expression of the dental material from the reservoir and through the cannula section, especially the cannula duct, and/or the functional element, especially the application element. The dispensing device may have a movable, plunger-like ram, which can be inserted through the opening of the cartridge base in order to press the plunger of the cartridge in the direction of the end face area of the reservoir. As a result, if the cannula duct is free, the dental material is pressed to the outside through the cannula duct. The discharge force for pressing out the dental material during a usual use is preferably in the range of about 100 N to 400 N, preferably in the range of 50 N to 400 N, and especially preferably in a range of 50 N to 250 N, and especially about 140 N. In particular, the cartridge base has a maximum external diameter that corresponds to the maximum external diameter of the cartridge at an end facing away from the cartridge. A reinforced end face area of the cartridge preferably has a maximum external diameter that corresponds to the maximum, external diameter of the cartridge base. As a result, the cartridge can be placed essentially horizontally on a horizontal plane concerning its longitudinal axis, as a result of which, for example, packaging of the cartridge is facilitated.

In particular, vent grooves extending in the direction of displacement of the plunger and/or in the longitudinal direction of the reservoir are provided on an inner surface of the preferably circular opening of the cartridge base. Air can escape from the reservoir due to the vent grooves during the insertion of the plunger to close the reservoir filled with the dental material. An extensively and especially completely air-free filling of the reservoir or of the cartridge with the dental material is made possible hereby. The air contained in the reservoir and displaced because of the plunger can escape laterally at the plunger to the outside during the insertion of the plunger.

According to a variant, a means for securing against rotation is provided at a cartridge base arranged facing away from the cannula section. The means for securing against rotation is preferably provided on an outer side of the reservoir to prevent rotation of the cartridge in a dispensing device. In particular, the means for securing against rotation has a positive-locking connection to prevent the cartridge from rotating about the longitudinal axis of the cartridge and/or of the reservoir. The means for securing against rotation may have a non-slip sleeve, which can be inserted into a mount of the dispensing device to hold the cartridge. In particular, the sleeve consists of an elastomer, a thermoplastic elastomer (TPE), a rubber material and/or a hard rubber material. The sleeve preferably consists of an elastomer, which is of the conventional nature, and can be processed by crosslinking and/or thermoplastically, especially reversibly. The sleeve is preferably connected to the cartridge base in a positive-locking manner to prevent the sleeve from rotating about the longitudinal axis of the cartridge. The means for securing against rotation and/or sleeve may interact with reinforcing struts of the cartridge, which extend in the longitudinal direction of the cartridge and/or of the reservoir in a middle area of the reservoir with reduced wall thickness. In particular, the mount of the dispensing device may be designed to mesh with the intermediate areas between the reinforcing struts. As an alternative, the means for securing against rotation may be molded integrally with the cartridge and/or the cartridge base as a third component within the framework of a multicomponent injection molding method, especially as a three-component injection molding method. The means for securing against rotation may be used, especially based on a color coding, as an information carrier for the dental material contained in the cartridge and/or for the intended use. As an alternative or in addition, a logo, a QR code and/or a lot number or batch number may be printed on the grip part.

According to another embodiment, a movable plunger, which has a first radius that corresponds to the inner radius of the reservoir at its first plunger end facing the reservoir and/or the dental material, is arranged in the reservoir for closing the reservoir and pressing the dental material out of the reservoir. The plunger is preferably movable by means of a plunger-like ram of a dispensing device in the direction of the cannula section. The first plunger end may have a conical shape. An area of the plunger facing away from the reservoir and/or from the dental material preferably has a reduced second diameter relative to the first radius. This leads, especially combined with vent grooves, to an enlarged passage for the escape of air during the insertion of the plunger to close the reservoir, and/or it is possible to save material when manufacturing the plunger. A second plunger end facing away from the first plunger end preferably has another radius, which corresponds to the first radius. In particular, the plunger is in contact with an inner surface of the cartridge and/or of the reservoir in the area of the first end and/or in the area of the second end. As a result, the reservoir can be closed with the plunger and/or the plunger is guided on the inner surface to press out the dental material. The first plunger end and the second plunger end preferably have an identical and/or mutually mirror-symmetrical design in relation to one another. As a result, the plunger can be inserted into the cartridge on both sides either with the first plunger end or with the second plunger end forward, as a result of which the effort needed for assembly is reduced.

According to another embodiment, which is also conceivable separately and independently from the present invention, the functional element is designed as a closing element for closing a cannula duct of the cannula section. The closing element has a plug part here, which is held in the cannula duct detachably, in a positive-locking and/or non-positive manner, especially by frictional engagement, and which fills the cannula duct at least partially for closing the cartridge. In particular, the plug parts fills the cannula duct completely. The plug part may have a length that corresponds at least to the length of the cannula duct. The plug part is preferably longer than the cannula duct, and the plug part exits from the cannula duct and/or the cartridge to the outside in connection with the cannula duct and projects over the cannula section and/or a free end of the plug part closes the cannula duct flush at the transition to the reservoir. The plug part may have a grip part, especially one designed as an information carrier, at a free end outside the cannula section and/or outside the cannula duct.

According to a variant, which is also conceivable separately and independently from the present invention, the functional element is designed as an application element for dispensing, burnishing, introducing and/or applying the dental material. The application element is preferably connected to the cartridge and/or the cartridge housing rigidly, especially nondetachably. In particular, the connection of the application element with the cartridge and/or with the cartridge housing is a positive-locking and/or non-positive connection. The outer circumferential surface and/or the outer contour of the application element may have an essentially rectangular, cuboid or spherical shape. The application element is manufactured, in particular, of a soft and/or elastic plastic material. In particular, the material of the application element has a hardness in the range of Shore-A or Shore-D, especially preferably in the range of 30 Shore A to 90 Shore A. In particular, the application element has one or more lips, with the lips preferably forming an outlet for the dental material. The soft and/or elastic application element permits gentle application of the dental material during a treatment. The distribution and/or the burnishing of the dental material is facilitated. Depending on the application, the application element may have different lengths in different cartridges. The risk of an undesired injury during a treatment is considerably reduced because of the soft and/or elastic material of the application element.

According to another embodiment, the application element has at least one elevation, especially a plurality of elevations, for detachably fixing a separate closing element on an outer surface of the application element. An separate closing element can thus be provided to close the cartridge and/or the application element. The closing element is connected here to the cartridge and/or to the application element detachably, especially such that it can be pulled off and/or screwed off. The elevations are preferably formed from the elastic material of the application element. A closing element pulled over the application element and the elevations can be fixed sufficiently by means of the elevations distributed preferably uniformly around the outer circumferential surface of the application element, so that the risk of an unintended separation of the closing element is reduced. The application element is preferably arranged partially on an outer side of the cartridge and/or of the cannula section. In particular, at least one cover area of the application element is arranged on an outer side of the cartridge and/or of the cannula section. The application element can thus extend at least partially on the outer side of the cartridge and/or of the cartridge housing by means of a cover area or of a plurality of cover areas. Because of the soft and/or elastic material of the application element and of the cover area, improved grip of the cartridge can be achieved hereby. Furthermore, the shape of the cover area may be used as a design element in order to obtain an esthetically attractive cartridge.

The application element preferably has an outlet for dispensing and/or applying the dental material. In particular, the outlet is arranged at an end of the application element facing away from the cartridge housing. The outlet may have a rectangular, square, round or oval cross section, especially in terms of its outer contour and/or inner contour. The application element preferably has a shape narrowing or expanding, especially conically, towards the outlet.

According to a variant, which is also conceivable independently and separately from the present invention, the application element has bristles. In particular, the bristles can be manufactured as part of the application element according to the multicomponent injection molding method. A subsequent application of fibers and/or an additional flocking can thus be avoided. The bristles preferably extend away from the outlet. In particular, the bristles extend, starting from the outlet, in parallel to one another and/or in an axial direction relative to a longitudinal axis of a cannula duct. The length and/or diameter of all bristles may be identical or at least partially different from one another. Different configurations of bristles that are very similar or different from one another in terms of length and/or thickness are thus conceivable. Greater softness and/or elasticity can be attained for the application element by means of the bristles. A treatment can be made more pleasant hereby for a patient. In particular, the distribution and/or burnishing of the dental material can be improved by means of the bristles.

According to another embodiment, which is also conceivable independently and separately from the present invention, the application element has a channel-like extension extending away from its outlet, especially for dispensing the dental material in a cavity and/or gingival pocket. The channel-like extension may have a sword-like design. In particular, the channel-like extension has at its free end a preferably obtuse-angled insertion part for insertion into a cavity and/or gingival pocket. A cavity and/or gingival pocket can be opened in a more pleasant manner for the patient by means of the free end of the insertion part made of a soft and/or elastic material. The insertion part preferably expands starting from the free end in the direction of the outlet and in terms of its width. In particular, a first area with a first width is provided at the free end of the insertion part, and a second area with a second width is provided at a spaced location from the free end in the direction of the outlet, the second width being greater than the first width. The channel-like extension with the first area and/or with the second area can be inserted into the cavity and/or gingival pocket during a treatment. More uniform distribution of the dental material is made possible by means of the first and/or second area compared to what is possible by means of a needle or cannula. As a result, the pain and/or pressure felt unpleasantly by the patient because of the introduced dental material is reduced. The risk of injury is considerably reduced because of the soft and/or elastic material of the application element.

The present invention will explained in more detail below on the basis of the following figures The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6a is a cut-away side view of the cartridge according to the present invention at one of different stages of filling;

FIG. 6b is a cut-away side view of the cartridge according to the present invention at different another of stages of filling;

FIG. 6c is a cut-away side view of the cartridge according to the present invention at different another of stages of filling;

FIG. 7 is a perspective side view of a fourth cartridge with a first application element as a functional element;

DESCRIPTION OF THE PREFERRED EMBODIMENTS

Figure 1:
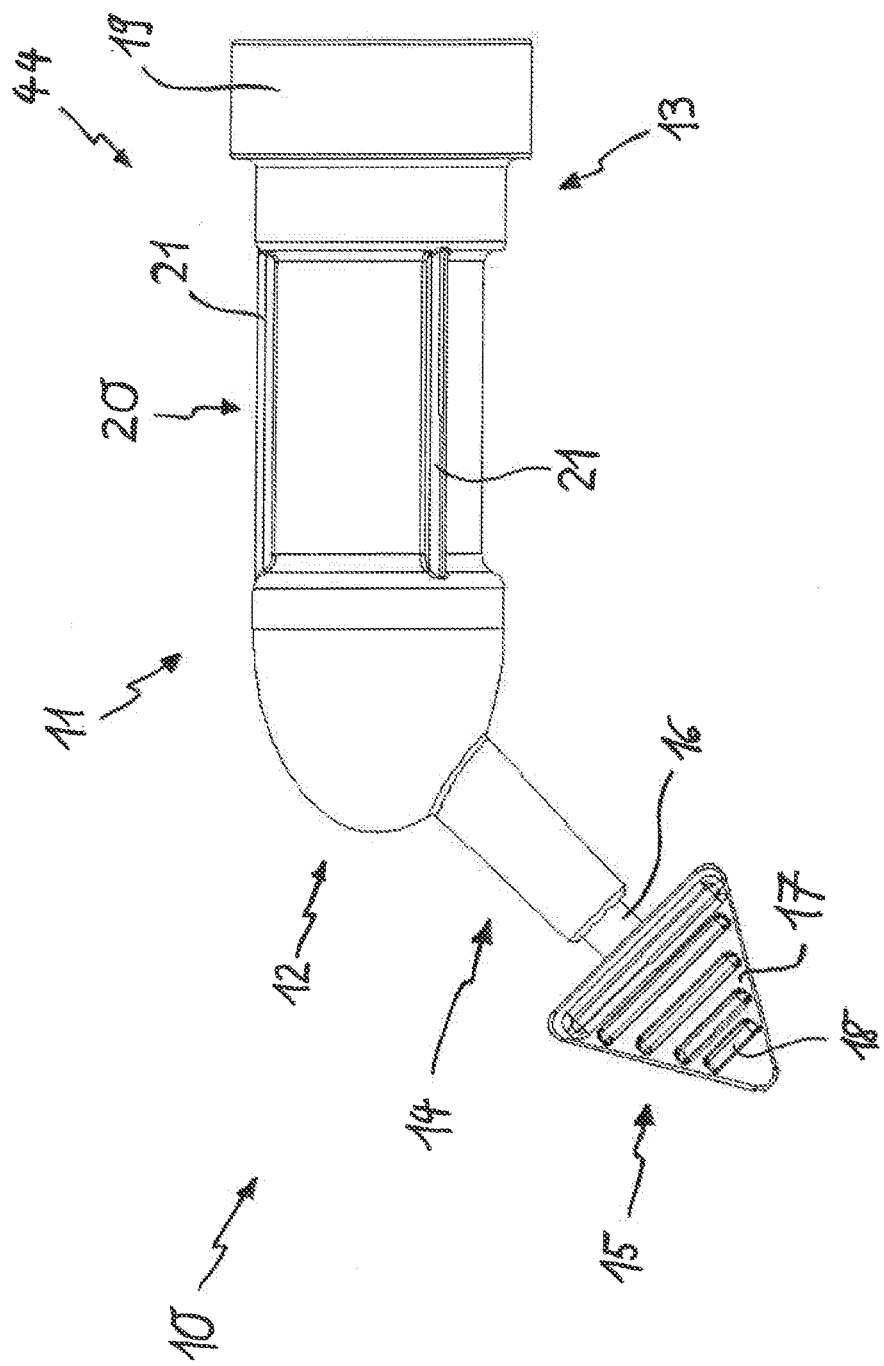
FIG. 1 is a side view of a first cartridge according to the present invention.

FIG. 1 shows a side view of a first cartridge 10 according to the present invention. The cartridge 10 has a reservoir 11 for containing a dental material, which is not shown here more specifically. The reservoir 11 is essentially tubular with a closed first end 12 and a second end 13, which faces away from the first end 12 and is open according to this view.

A cannula section 14 is associated with the first end 12 of the reservoir 11. The cannula section 14 has a tubular design in this exemplary embodiment. The longitudinal axis of the cannula section 14 is directed at right angles to the longitudinal axis of the reservoir. The angle between the longitudinal axis of the reservoir 11 and the longitudinal axis of the cannula section 14 is approx. 45° in this example. As an alternative, the angle is in the range of 40° to 60°. The cannula section 14 is made in one piece with the reservoir 11.

A functional element 15 is associated with the cannula section 14. The functional element 15 has a cylindrical plug part 16, which is arranged extensively within the cannula section 14, and a section of the plug part 16 projects to the outside from the end of the cannula section 14 facing away from the reservoir 11 in this exemplary embodiment.

Furthermore, the functional element 15 has a grip part 17 for grasping the functional element 15 by a person. The grip part 17 is arranged on the section of the plug part 16 projecting from the cannula section 14 and is made in one piece with the plug part 16 in this exemplary embodiment. The functional element 15, which is designed here as an example as a closing element for the reservoir 11, and the plug part 16 can be pulled out of the cannula section 14 by means of the grip part 17.

The grip part 17 is designed here as an example as a triangular plate. As an alternative, other shapes of the grip part 17 are conceivable, for example, as a tetragonal, pentagonal, hexagonal, polygonal, circular or elliptic plate or in an essentially cylindrical, conical, spherical, elliptic shape, etc. The grip part 17 has a plurality of ribs 18 in this exemplary embodiment, which increase the grip of the grip part 15. Not all ribs 18 are provided with a reference number for clarity's sake.

Based on the shape of the grip part 17 as a function of the type of the dental material in the reservoir 11, the grip part 17 is used as an information carrier for the contents and/or the intended use of the cartridge 10.

A cartridge base 19 is associated with the second end 13 of the reservoir 11. The cartridge base 19 has an essentially ring-shaped design and is used to arrange the cartridge 10 in a dispensing device, not shown here more specifically. A cylinder or a plunger-like ram can moved by means of the dispensing device in the longitudinal direction of the cartridge 10 or of the reservoir 11 into the reservoir 11, as a result of which the dental material can be dispensed to the outside from the reservoir 11 and through the cannula section 14 with the functional element 15 removed.

A cartridge housing 44 is formed from the reservoir 11, the cannula section 14 and the cartridge base 19.

The wall thickness of the cartridge 10 is reduced in a middle area 20 of the reservoir 11 relative to the wall thickness of the reservoir 11 outside the middle area 20, as a result of which material is saved. The outer surface of the reservoir 11 is offset inwardly in the middle area 20 in relation to the outer surface outside the middle area 20. Reinforcing struts 21 are arranged in the middle areas 20 in the longitudinal direction of the cartridge 10 and of the reservoir 11.

The reinforcing struts 21 extend in the longitudinal direction of the cartridge 10 and of the reservoir 11 and are used to additionally reinforce the middle area 20. As a result, sufficient stability can be attained even in case of a reduction of the wall thickness in the middle area 20. Three reinforcing struts 21 are arranged uniformly in relation to one another around the outer circumference of the middle area 20 in this exemplary embodiment. As an alternative, a single reinforcing strut 21 or two, four, five, six or more reinforcing struts 21 are also conceivable.

Figure 2:
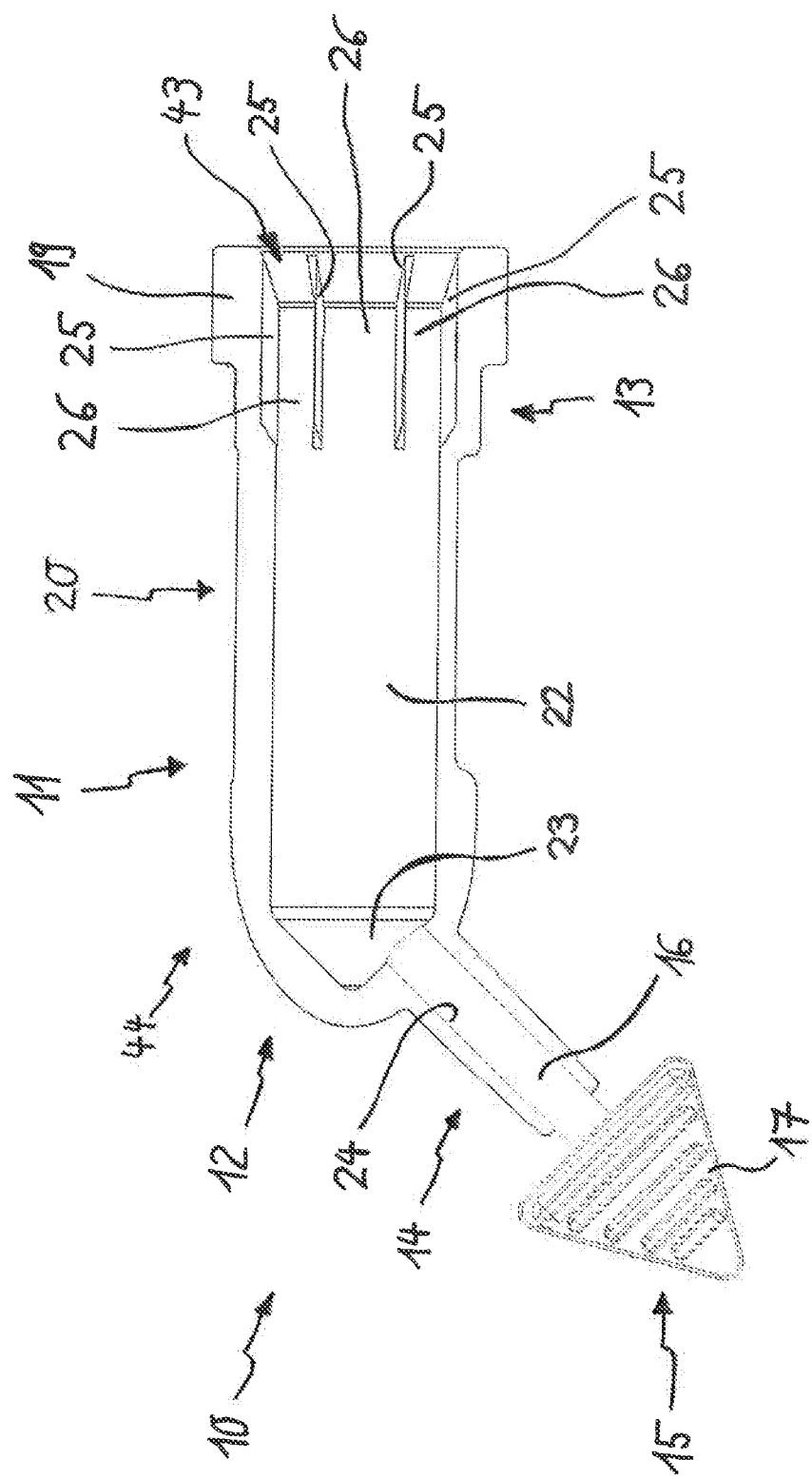
FIG. 2 is a cut-away side view of the first cartridge according to the present invention according to FIG. 1.

FIG. 2 shows a cut-away side view of the cartridge 10 according to the present invention according to FIG. 1. The reservoir 11 has a cylindrical inner space 22, and the cylindrical inner space passes over into a conical plunger mount 23 in the area of the first end 12.

A cannula duct 24 of the cannula section 14 is connected to the reservoir 11 in the area of the plunger mount 23. The cannula duct 24 is filled and closed with the plug part 16 of the functional element 15 over its entire length in this exemplary embodiment. A dental material, not shown here in more detail, thus cannot enter the cannula duct 24 from the reservoir 11.

Webs 26 are provided in the area of the second end 13 of the reservoir 11 and of the cartridge base 19. The webs 26 are directed in the longitudinal direction of the cartridge 10 and of the reservoir 11 and are distributed at uniformly spaced locations from one another on the inner surface of an opening 43 of the essentially ring-shaped cartridge base 19. In relation to the longitudinal axis of the reservoir 11, the webs 26 only extend in the radial direction to the extent that the barrier-free diameter of the inner space 22 of the reservoir 11 is continued in the area of the webs 26. The inner space 22 of the reservoir thus continues in the area of the second end 13 and of the cartridge base 19 without this space being compromised because of the webs 26. Vent grooves 25, whose function will be explained in more detail below, are formed between the webs 26. The webs 26 are made broader in this exemplary embodiment than the vent grooves 25. As an alternative, the positions and/or the width of the webs 26 and of the vent grooves 25 may be transposed, so that the reference numbers 26 designate the vent grooves and the reference numbers 25, the webs.

Figure 3:
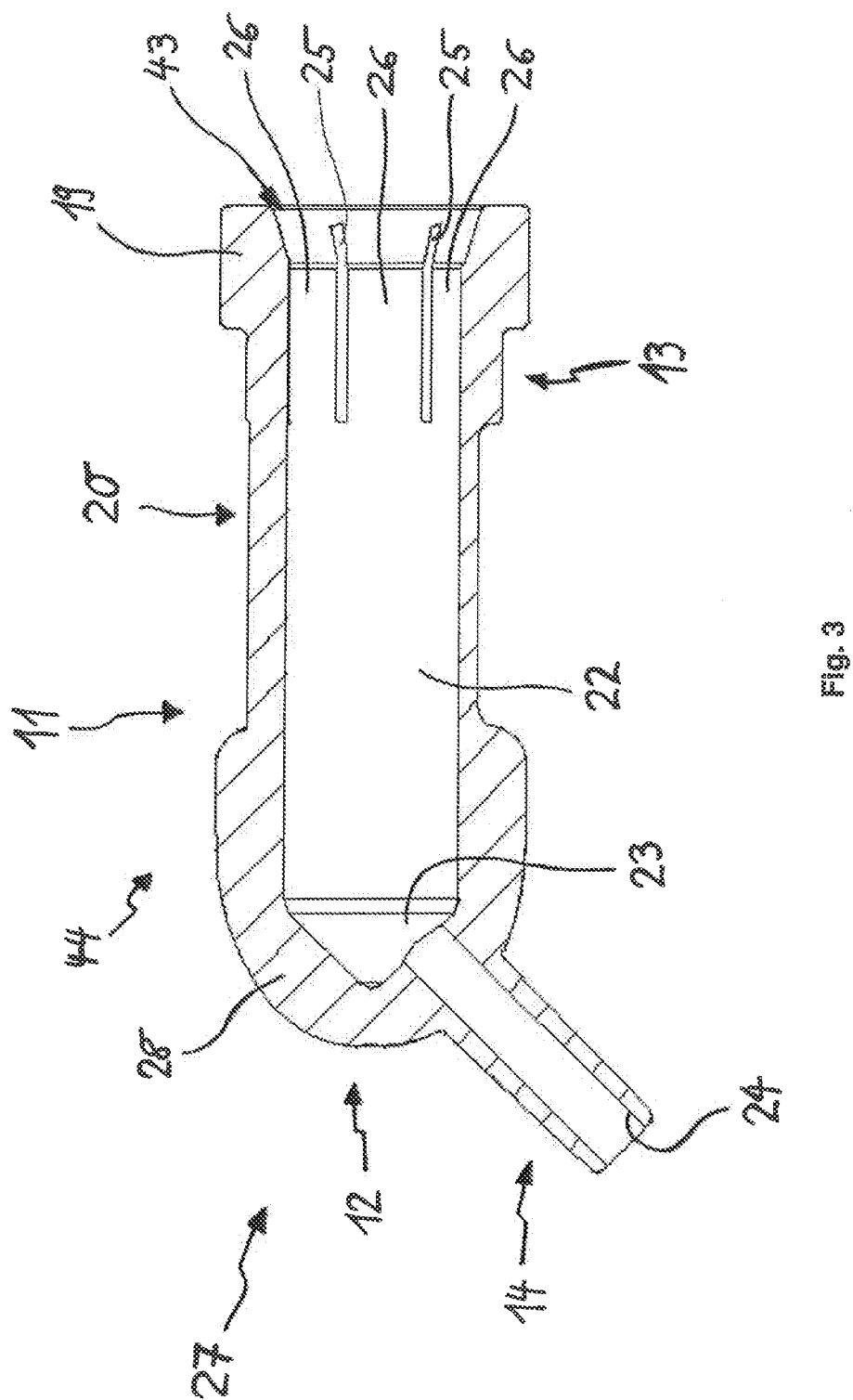
FIG. 3 is a cut-away side view of a second cartridge.

FIG. 3 shows a cut-away side view of a second cartridge 27. The design of the cartridge 27 corresponds extensively to that of the cartridge 10. Reference will therefore be made to the above description. The cartridge 27 is shown without the functional element 15 here. Unlike the cartridge 10, the cartridge 27 is reinforced in the area of the first end 12 of the reservoir 11 and relative to the second end 13. The wall thickness is greater in the area of the first end 12 and in an end face area 28 of the cartridge 27 and/or of the reservoir 11 than in the area of the second end 13 of the reservoir 11 and of the cartridge 27.

When pressing a dental material, not shown more specifically here, out of the reservoir 11 through the cannula section 24, a force of pressure acts in the longitudinal direction of the cartridge 27 and of the reservoir 11 and in the direction of the first end 12 and the end face area 28. The forces of pressure occurring can be absorbed and transmitted because of the reinforced design in the end face area 28 and a greater wall thickness in the end face area 28, and the risk of damage to the cartridge 27 is considerably reduced even in case of unusually strong forces.

Figure 4:
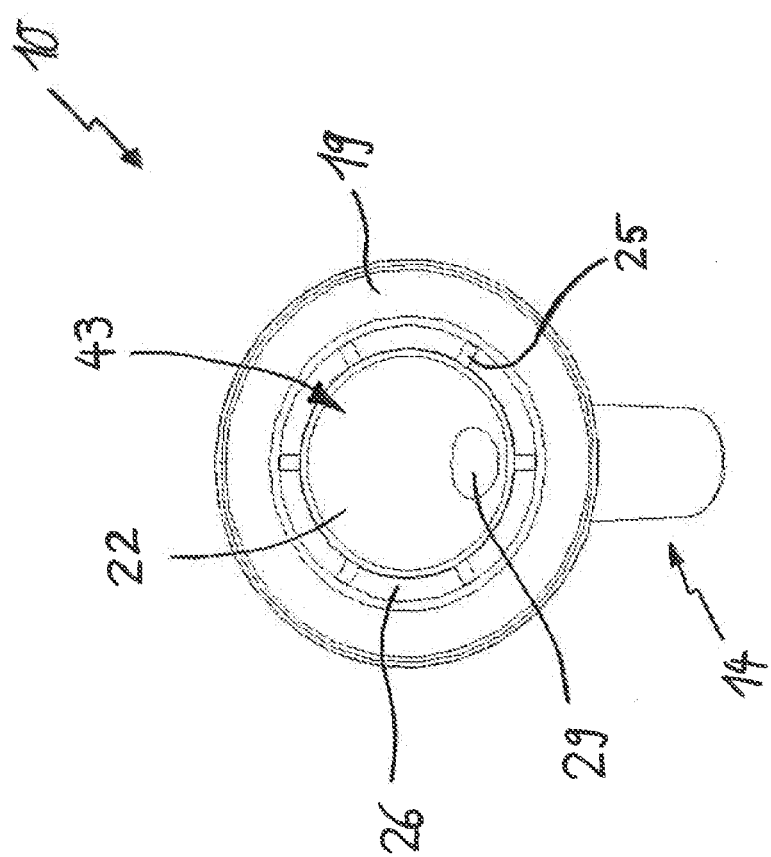
FIG. 4 is a rear view of the cartridge according to the present invention according to FIG. 1.

FIG. 4 shows a rear view of a cartridge 10 according to the present invention according to FIG. 1 without the functional element 15, wherein the following descriptions analogously apply to all cartridge designs according to this description. Six webs (26) are arranged distributed at uniformly spaced locations from one another on the inner surface of the cartridge base 19. Six vent grooves 25 are correspondingly distributed here uniformly on the inner surface of the cartridge base 19. As an alternative, fewer or more webs 26 and vent grooves 25 are also conceivable. Not all webs 26 and vent grooves 25 are provided with a reference number for the sake of greater clarity.

The ring-shaped cartridge base 19 and the webs 26 are directed coaxially in relation to the longitudinal axis of the essentially cylindrical inner space 22. The webs 26 extend here inwardly up to the outer circumference of the inner space 22, so that the diameter of the inner space 22 remains barrier-free even in the area of the second end 13 and of the cartridge base 19.

In the unfilled and unclosed state of the cartridge 10 shown here, an opening 29 can be seen, with which the inner space 22 is in connection with the cannula duct 24 of the cannula section 14.

Figure 5:
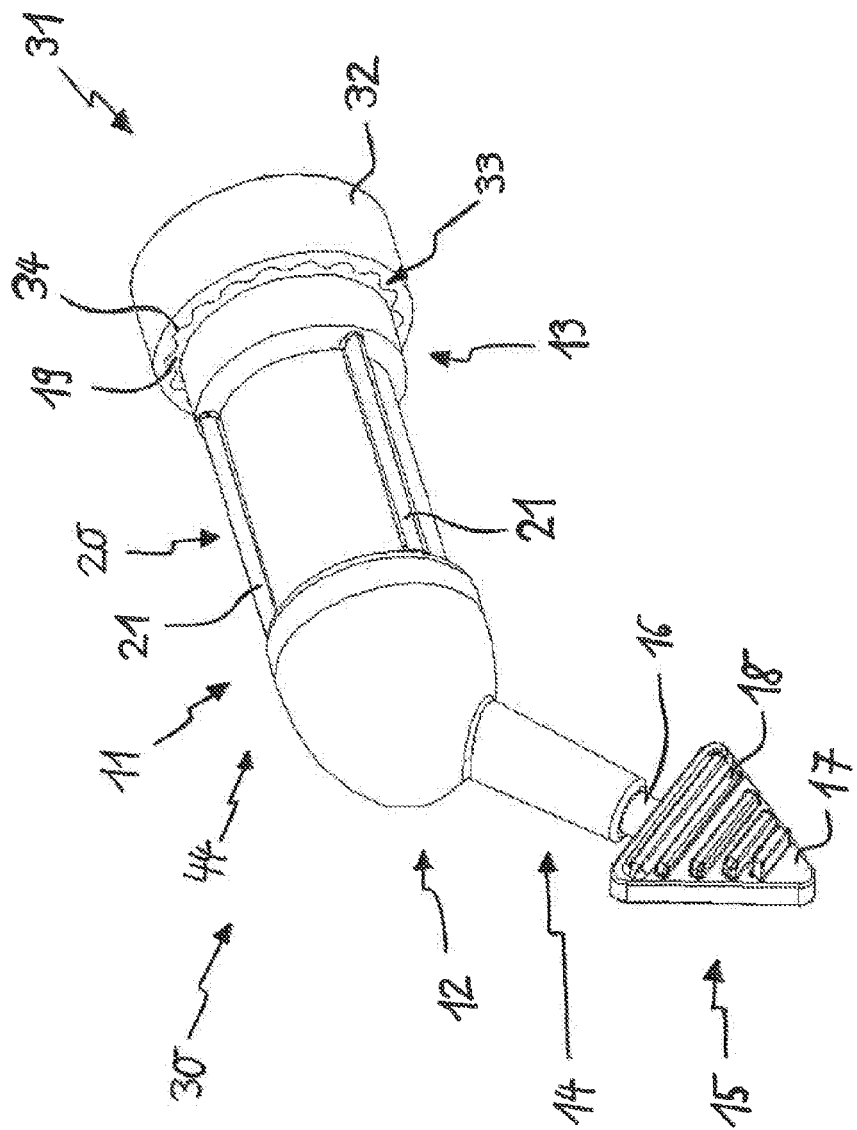
FIG. 5 is a perspective side view of a third cartridge according to the present invention with a means for securing against rotation.

FIG. 5 shows a perspective side view of a third cartridge 30 according to the present invention with a means for securing against rotation 31. The design corresponds extensively to that of the cartridge 10. Reference will therefore also be made to the preceding description. The means for securing against rotation 31 is associated with the cartridge base 19 in this exemplary embodiment.

A sleeve 32 is arranged around the outer circumferential surface of the cartridge base 19. The sleeve 32 is made here of an elastomer as an example. Furthermore, the sleeve 32 is connected to the cartridge base 19 by means of a positive-locking connection 33, wherein the connection 33 prevents the sleeve 32 from rotating about the longitudinal axis of the cartridge 30 and of the reservoir 11.

The outer circumferential surface of the cartridge base 19 has a ring-shaped wave profile 34 for this in this exemplary embodiment. The longitudinal axes of the wave peaks and wave troughs of the wave profile 34 are directed here in the longitudinal direction or parallel to the longitudinal axis of the cartridge 30 and of the reservoir 11. The inner surface of the sleeve 32 has a wave profile 34 having a shape corresponding to the wave profile 34. As a result, the sleeve 32 can be pushed over the cartridge base 19 in the longitudinal direction of the cartridge 30 and of the reservoir 11, but rotation of the cartridge 30 in relation to the sleeve 32 about the longitudinal axis of the cartridge 30 and of the reservoir 11 is prevented from occurring in the mounted state. As an alternative, the sleeve 32 can be molded integrally with the cartridge base 19 within the framework of a multicomponent injection molding method, especially a three-component injection molding method. In case the material is selected suitably and/or the adhesion between the sleeve 32 molded integrally and the cartridge base 19 is sufficient, a wave profile 34 may also be eliminated in this case.

The cartridge base 19 and the sleeve 32 are dimensioned such that the cartridge base 19 can be received and plugged in a usual mount of a dispensing device, not shown here, together with the sleeve 32. The risk of rotation of the cartridge 30 in the mount of the dispensing device about the longitudinal axis of the cartridge 30 and of the reservoir 11 is considerably reduced due to the non-slip or friction-tight design of the sleeve.

FIGS. 6a-6f show cut-away side views of the cartridge 10 according to the present invention in different stages of filling, wherein the following views analogously apply to all cartridge designs according to this description.

FIG. 6a shows the cartridge 10 with the functional element 15, which is inserted into the cannula section 14 and completely fills the cannula duct 24, so that the opening 29 is closed. The cartridge 10 is designed as a first component and the functional element 15 as a second component of a two-component injection-molded part. The two-component injection-molded part is manufactured from polybutylene terephthalate in this exemplary embodiment.

The second end 13 of the reservoir 11 and the ring-shaped cartridge base 19 are open. The inner space 22 of the reservoir 11 is thus accessible. The cartridge 10 is aligned such that the longitudinal axes of the cartridge 10 and of the reservoir 11 are essentially at right angles.

FIG. 6b shows that a filling tube 35 is inserted into the inner space 22 through the open cartridge base 19 and the open end 13 for filling the cartridge 10. After insertion of the filling tube 35, a dental material 36 is released into the inner space 22. The inner space 22 is being filled starting from the first end 12 in the direction of the second end 13.

FIG. 6c shows the cartridge 10 filled with the dental material 36. Nearly the entire inner space 2 is filled with the dental material 36. The filling tube 35 is removed. A free residual volume 37 is left only in the area of the second end 13 of the reservoir 11.

Figure 6F:
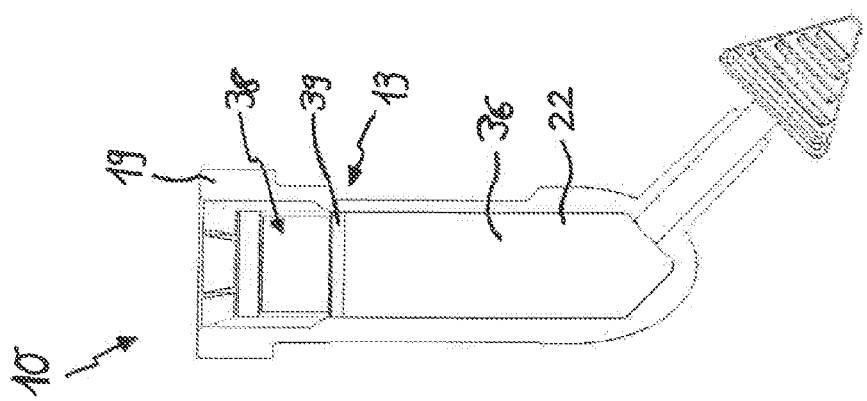
FIG. 6f is a cut-away side view of the cartridge according to the present invention at different another of stages of filling.
Figure 6E:
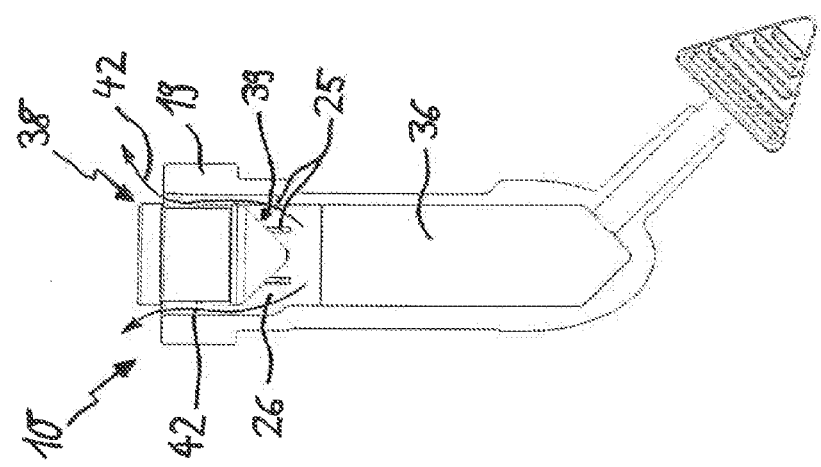
FIG. 6e is a cut-away side view of the cartridge according to the present invention at different another of stages of filling.
Figure 6D:
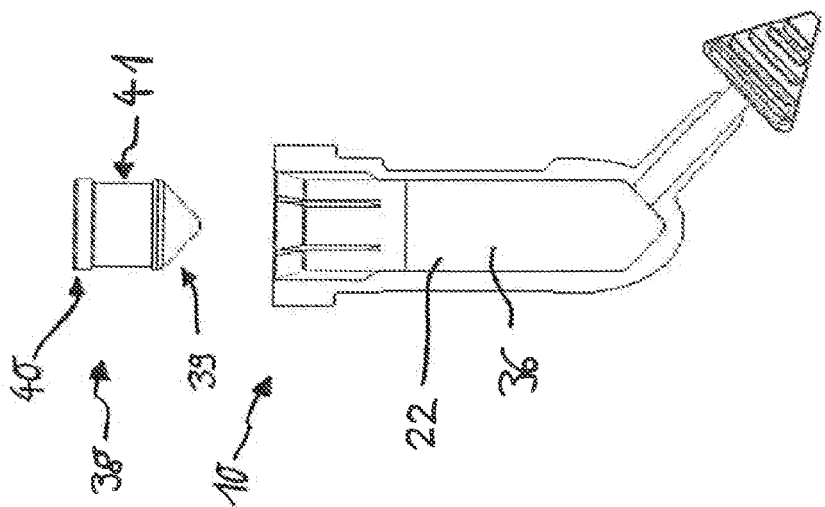
FIG. 6d is a cut-away side view of the cartridge according to the present invention at different another of stages of filling.

FIG. 6d shows the cartridge 10 with the plunger 38 provided for the cartridge 10. The plunger 38 has a conical first plunger end 39, which faces the cartridge 10 and the cartridge base 19. The first plunger end 39 has a maximum radius or outer circumference, which corresponds to the inner radius of the reservoir 11 and of the inner space 22. A second plunger end 40 facing away from the first plunger end 39 likewise has a radius or outer circumference that corresponds to the inner radius of the reservoir 11 and of the inner space 22 in this exemplary embodiment. A middle area 41 of the plunger between the first plunger end 39 and the second plunger end 40 has a reduced radius and reduced outer circumference compared to the maximum radius and outer circumference of the first plunger end 39 and of the second plunger end 40.

It can be seen in FIG. 6e that the plunger 38 is inserted into the cartridge 10 with the conical first plunger end 39 forward through the ring-shaped cartridge base 19. The plunger 38 now slides in the area of the cartridge base 19 along the webs 26. The air still present in the cartridge 10 and the reservoir 11 flows around the plunger 38 during the insertion of the plunger 38 and to the outside from the cartridge base 19 through the vent grooves 25, as this is schematically indicated by arrows 42.

FIG. 6f shows the cartridge 10 with the plunger 38 in its end position for closing the cartridge 10 and the reservoir 11. The conical first end 39 is nearly completely immersed into the inner space 22 and the dental material 36. The ring-shaped component of the first conical end 39 is in contact with the inner surface of the reservoir 11, sealing the inner space 22. Because of the conical shape of the first conical end 39 and the vent grooves 25, an at least approximately air-free filling of the inner space 22 with the dental material 36 is carried out. The cartridge 10 is now ready for the usual use with a dispensing device. All working steps for filling the cartridge 10 and the insertion of the plunger 38 according to FIGS. 6a through 6f can be carried out in a fully automated manner.

FIG. 7 is a perspective side view of a fourth cartridge 45, in which the functional element 46 is designed as a first application element 46 for dispensing and applying the dental material. Features that are identical to the preceding ones have the same reference numbers. Reference is therefore also made to the preceding description. The application element 46 is rigidly connected to the cartridge housing 44 and the cannula section 14 in this exemplary embodiment. The application element 46 and the cannula section 14 are connected to one another so rigidly in this exemplary embodiment that detachment of the application element 46 is prevented from occurring without destruction. The application element 46 consists of an elastic plastic material, so that the application element 46 is soft and flexible. The application element 46 is formed from a thermoplastic elastomer in this exemplary embodiment.

The application element 46 forms an extension of the cannula section 14 and has an outlet 47 for the discharge of the dental material to the outside. The outlet 47 is arranged at a free end of the application element 46 and faces away from the reservoir 11. The outlet 47 has a rectangular cross section here as an example. As an alternative, other cross sections, for example, a square, round or oval cross section, are also conceivable here. The cross section of the port of the application element 46 to the cannula section 14 corresponds essentially to the cross section of the cannula section 14, which is round here as an example concerning its outer circumference. The cross section of the application element 46 thus changes continuously and starting from the cannula section 14 in the direction of the outlet 47.

The application element 46 has a plurality of cover areas 48 in this exemplary embodiment, which are arranged on the outer side of the cartridge housing 44, here of the cannula section 14. The cover areas 48 lie on the outer side of the cannula section 14 and are rigidly connected to the outer side of the cannula section 14. The cover areas 48 have a web-like design here and extend from the application element 46 in the axial direction or the cannula section 14 to the reservoir 11. Four web-like cover areas 48 are arranged essentially distributed uniformly around the cannula section 14 in this exemplary embodiment.

Furthermore, the application element 46 has a plurality of elevations 49 in this exemplary embodiment, which rise outwardly starting from the outer surface of the application element 46. An elevation 49 each is arranged here as an example at the outer end of the web-like cover area 48. The elevations 49 are used to detachably fasten a closing cap, which is not shown more specifically here and can be pulled over the application element 46 to close the outlet 47. Based on the elevations 49 made of the soft and elastic material of the application element 46, a sufficiently firm seating of the closing cap can be achieved. The elevations 49 are designed here as knobs as an example.

Figure 8:
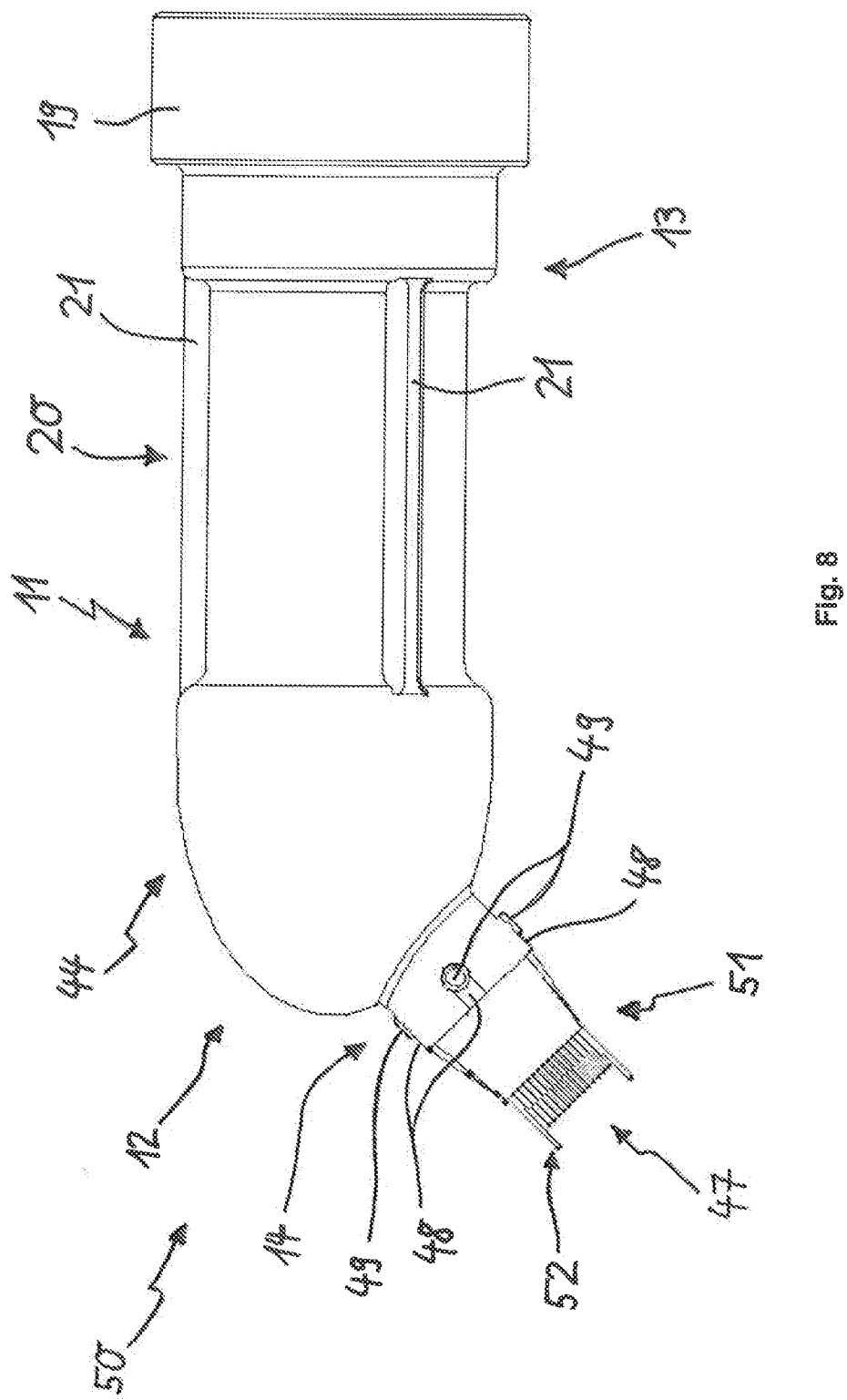
FIG. 8 is a side view of a fifth cartridge with a second application element as a functional element.

FIG. 8 shows a side view of a fifth cartridge 50, in which a functional element 51 is designed as a second application element 51. Features identical to those described above have the same reference numbers. Reference is therefore also made to the preceding description. The second application element 51 extensively corresponds to the first application element 46 according to FIG. 7. In addition, a plurality of bristles 52 are provided in the second application element 51.

The bristles 52 are made in one piece with the application element 51 in this exemplary embodiment. Furthermore, the bristles 52 extend, for example, in the axial direction of the cannula section 14 here and are arranged essentially in parallel to one another.

Figure 9:
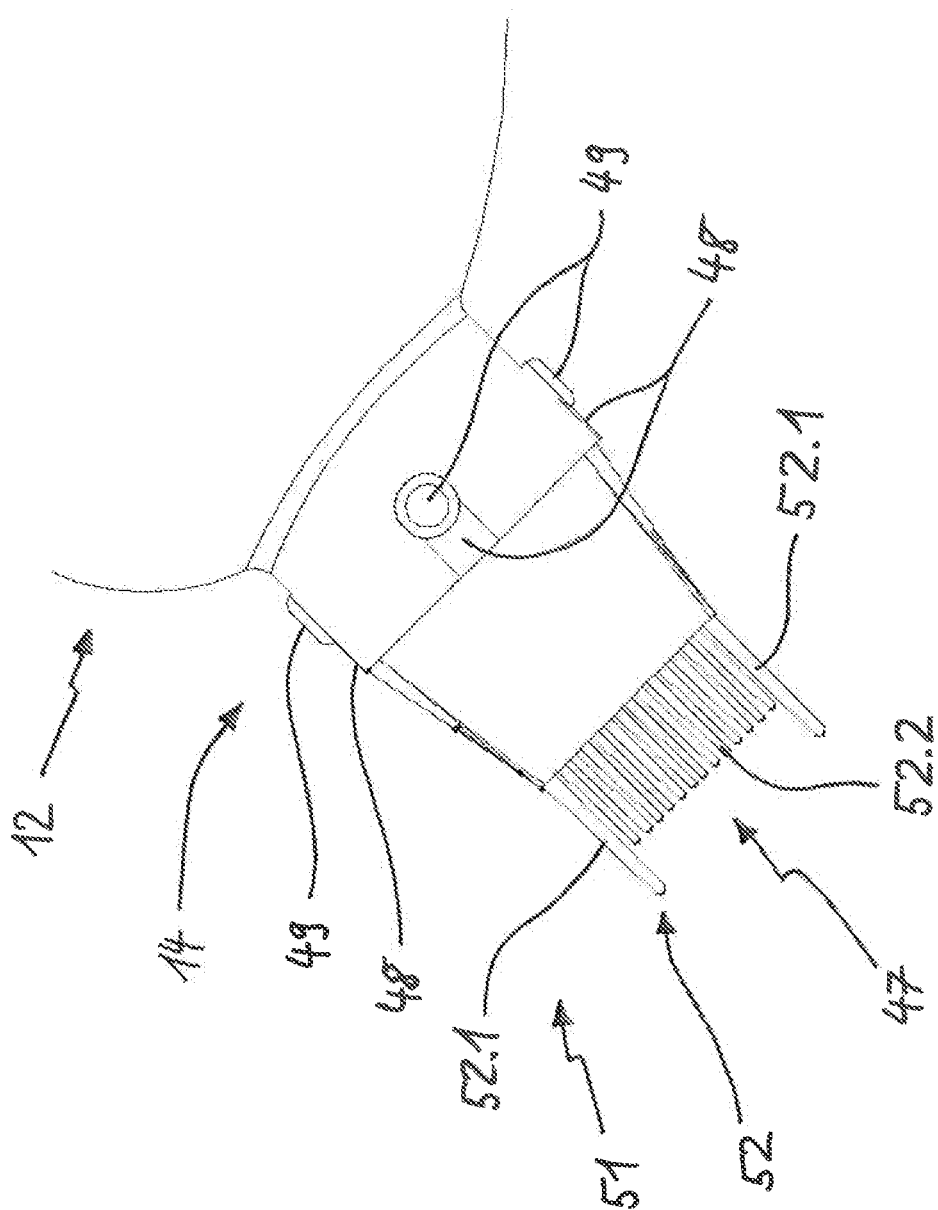
FIG. 9 is a detail of the side view of the fifth cartridge with the second application element according to FIG. 8.

FIG. 9 shows a detail of the side view of the fifth cartridge 50 with the second application element 51 according to FIG. 8. Two different types of bristles 52, namely, first bristles 52.1 and second bristles 52.2, which differ in their length and their diameter, are provided in this exemplary embodiment. The first bristles 52.1 are longer, for example, than the second bristles 52.2. Furthermore, the first bristles 52.1 have a larger diameter than the second bristles 52.2. The first bristles 52.1 are arranged at two edges of the outlet 47, which are arranged essentially in parallel to one another, while the second bristles 52.2 are arranged at edges of the outlet 47 that are directed essentially at right angles to the edges with the first bristles 52.1. As an alternative to the exemplary embodiment being shown here, any desired arrangements of bristles of a very similar design and/or of a plurality of bristles having different designs are conceivable.

Figure 10:
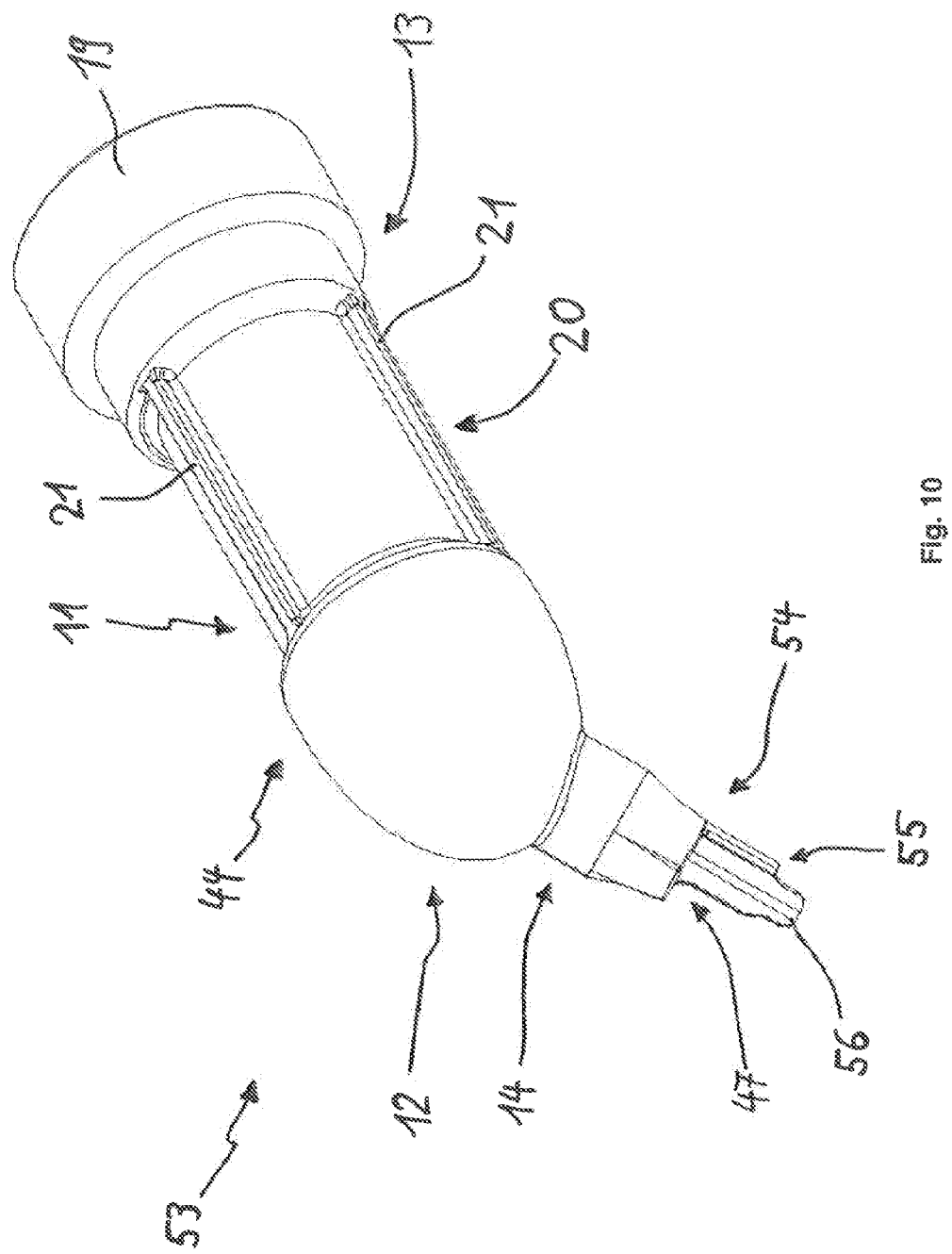
FIG. 10 is a perspective side view of another cartridge with another application element as a functional element.

FIG. 10 shows a perspective side view of another cartridge 53, in which a functional element 54 is designed as another application element 54. Features identical to the previous ones are designated by the same reference numbers. Reference is therefore also made to the preceding description. The additional application element 54 corresponds in many parts to the first application element 46 according to FIG. 7. Even though no cover areas 48 or elevations 49 are provided in the application element 54 in this exemplary embodiment, one or more cover areas 48 or elevations 49 are conceivable in the application element 54 as well. In addition, the additional application element 54 has a channel-like extension 55.

The channel-like extension 55 extends, starting from the outlet 47, in the axial direction of the cannula section 14. The channel-like extension 55 is designed to transmit and guide the dental material, which is being discharged from the outlet 47. The channel-like extension 55 is formed in this exemplary embodiment by two projections of the outlet 47, which are arranged essentially at right angles to one another.

At its free end facing away from the outlet 47, the channel-like extension 55 has an insertion part 56. The insertion part 56 has an obtuse angle in this exemplary embodiment and is used to insert the application element 54 into a cavity or gingival pocket, not shown more specifically here. The insertion part 56 has a first maximum width in a first area of its free end. The insertion part 56 expands at a spaced location from the free end and in the direction of the outlet 47 to a second area with a greater width. The insertion part 56 has a second maximum width in the second area, and the second maximum width is greater than the first maximum width. Because of the larger surface of the insertion part 56 in the second area, the dental material can be introduced into a cavity and/or gingival pocket over a large surface.

Figure 11:
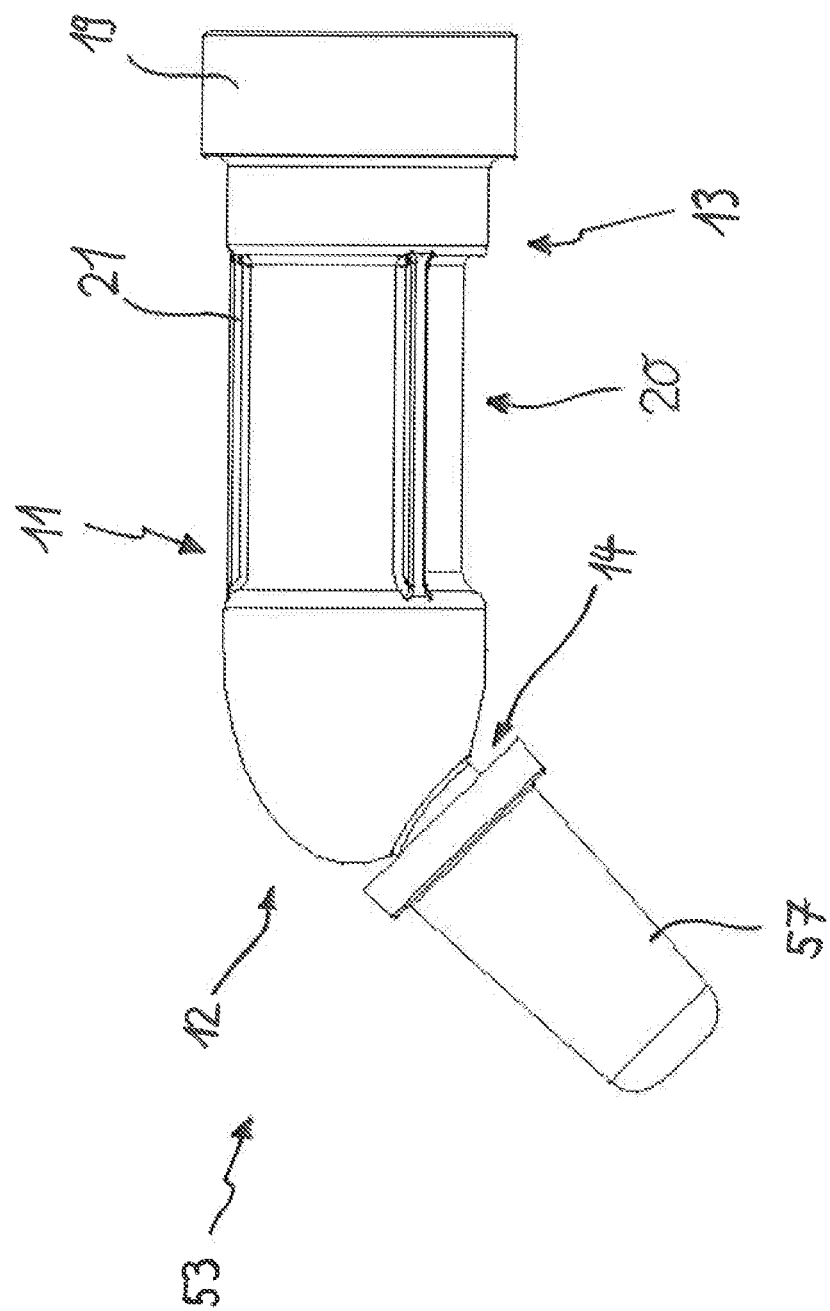
FIG. 11 is a side view of a cartridge according to FIG. 10 with a closing cap attached.

FIG. 11 shows a side view of a cartridge 53 according to FIG. 10 with an attached closing cap 57. The closing cap 57 is pulled here, for example, over the additional application element 54. As an alternative, the closing cap 57 may be provided for closing any desired application element. In particular, the closing cap 57 is provided for the cartridge 45 with the first application element 46 or for the cartridge 50 with the second application element 51.

The closing cap 57 fully encloses the additional application element 54. The closing cap 57 is pulled for this over the additional application element 54. The additional application element 54 is protected hereby during transportation and during storage. In addition, the outlet 47 is closed by means of the closing cap 57. The closing cap 57 is attached to the cannula section 14 in the area of said cannula section 14 and is detachably connected to the cannula section 14 and the cartridge 53.

Figure 12:
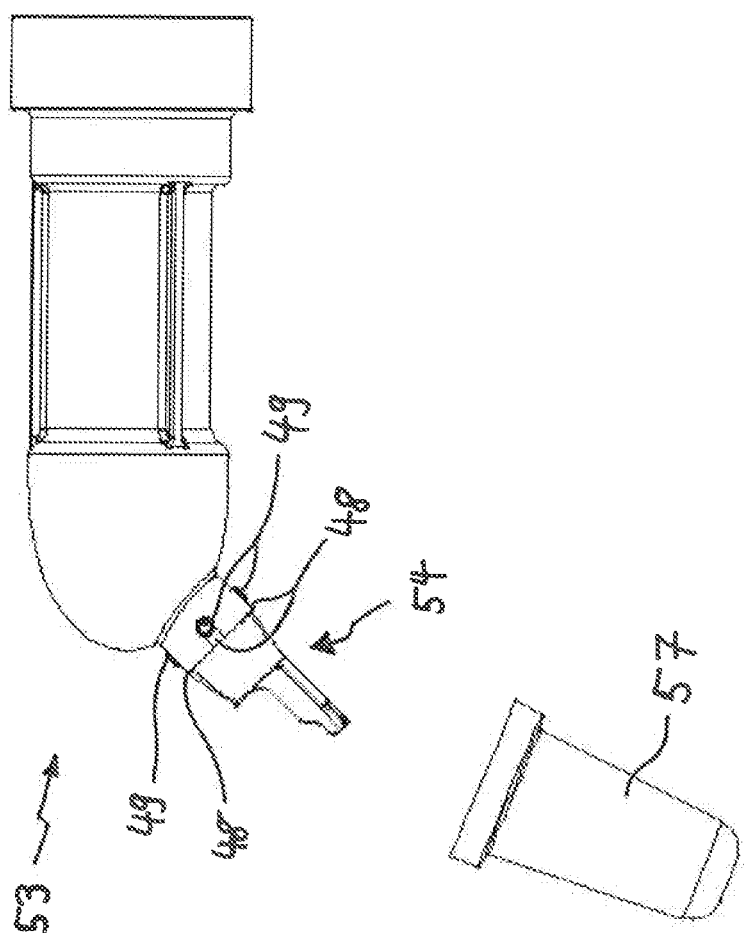
FIG. 12 is a side view of the cartridge according to the present invention according to FIG. 10 with the other application element and a closing cap pulled off.

FIG. 12 shows a side view of the cartridge 53 according to the present invention according to FIG. 10 with the additional application element 54 and with a closing cap 57 pulled off. The additional application element 54 has a cover area 48 and elevations 49 in this exemplary embodiment. The elevations 49 are used here to detachably fix the closing cap 57 with the cartridge 53.

Figure 13:
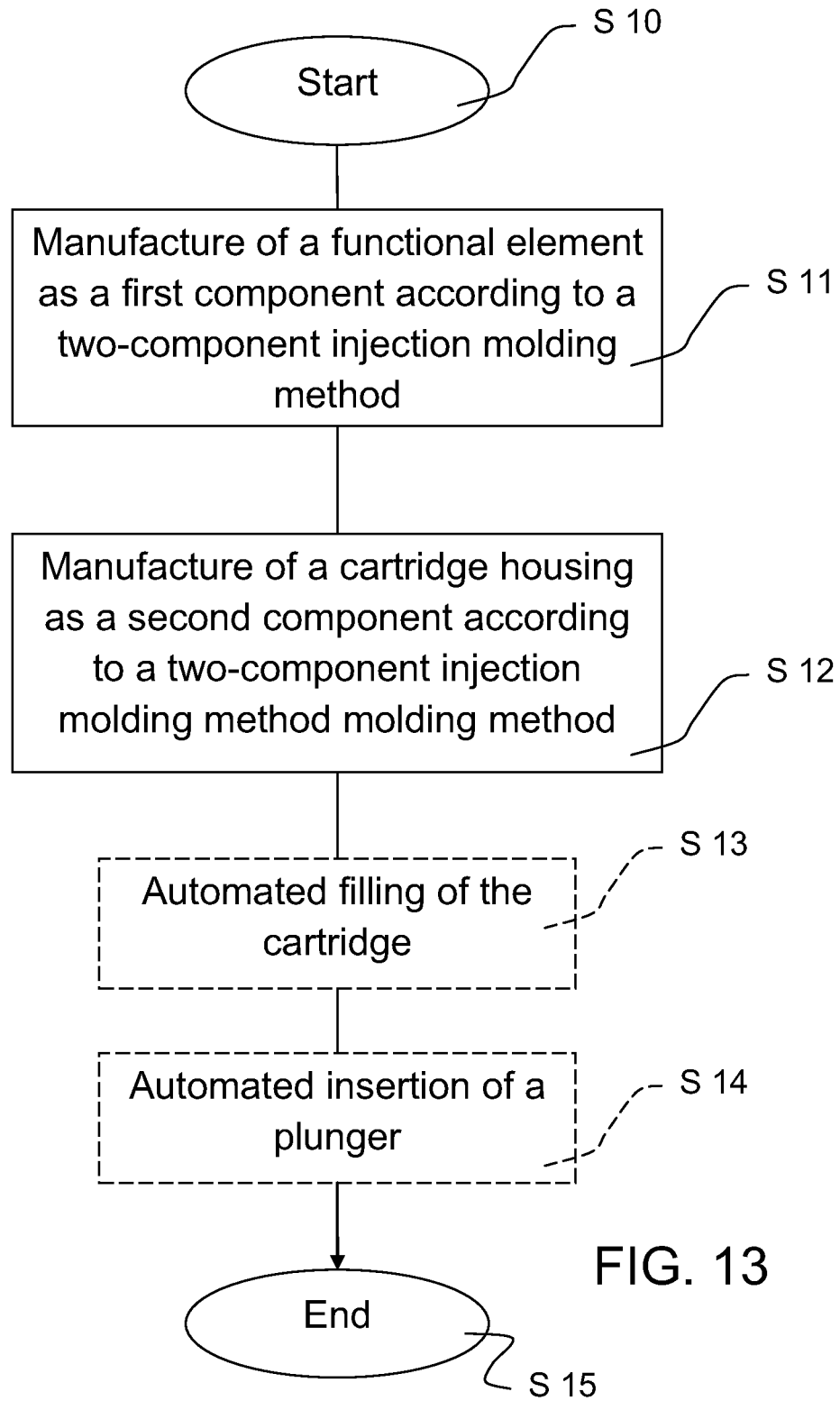
FIG. 13 is a first schematic flow chart of a method according to the present invention.

FIG. 13 shows a first schematic flow chart for a first method according to the present invention. The method for manufacturing a cartridge 10, 27, 30, 45, 50, 53 is started in a step S10. A first component is then manufactured in a step S11 according to a two-component injection molding method. The functional element 15, 46, 51, 54 is manufactured here as a first component.

A second component is then manufactured in a step S12 according to the two-component injection molding method, a cartridge housing 44 comprising the reservoir 11, the cannula section 14 and the cartridge base 19 being manufactured here as the second component. For example, the second component can be manufactured and molded at least partially around the first component.

In the case of the functional element 15, the cannula section 14 can be manufactured around the plug part 16 of the functional element 15, the plug part 16 completely filling the cannula duct 24. The plug part 16 is held in the cannula duct 24 in a positive-locking and frictionally engaged manner. The connection between the circumferential surface of the plug part 16 and the inner surface of the cannula duct 24 is detachable here. To close the cannula section 14, the functional element 15 has exclusively the cylindrical plug part 16, which has an external diameter that corresponds to the internal diameter of the cannula duct 24 and is arranged within the cannula duct 24. The plug part 16 can be pulled out of the cannula duct 24 by pulling the plug part 16 by means of the grip part 17.

In case of a cartridge 45, 50, 53, the functional element 46, 51, 54 is rigidly connected to the cartridge 45, 50, 53, and the functional element 46, 51, 54 is prevented from being able to be detached from the cartridge 45, 50, 53 without destruction.

The method can subsequently be ended with a step S15. As an alternative, steps S13 and S14 may, however, be carried out between the step S12 and step S15. The cartridge 10, 27, 30, 45, 50, 53 is filled in an automated manner according to step S13, and a plunger 38 is subsequently inserted into the cartridge 10, 27, 30, 45, 50, 53 according to step S14 to close the inner space 22 of the reservoir 11. The filling and the insertion of the plunger 38 are carried out as described above on the basis of FIGS. 6*a* through 6*f.*

Thus, a fully automated manufacturing process for manufacturing the cartridge 10, 27, 30, 45, 50, 53 can be attained.

In addition, reclosing of the cannula duct 24 after a first-time use of the cartridge 10, 27, 30 is made considerably difficult because of the shape of the functional element 15 with the plug part 16 compared to caps commonly used hitherto. Due to the dental material 36 entering the cannula duct 24 during a first-time use, inserting the plug part 16 into the cannula duct 24 already filled with the dental material 36 is considerably hindered or is even ruled out completely. The risk of a further use of residues of the dental material 36 after a first use of the cartridge 10, 27, 30 is considerably reduced hereby.

The application and/or burnishing of a dental material 36 can be carried out considerably more easily, effectively and more pleasantly for a patient by means of the functional elements 46, 51, 54.

Figure 14:
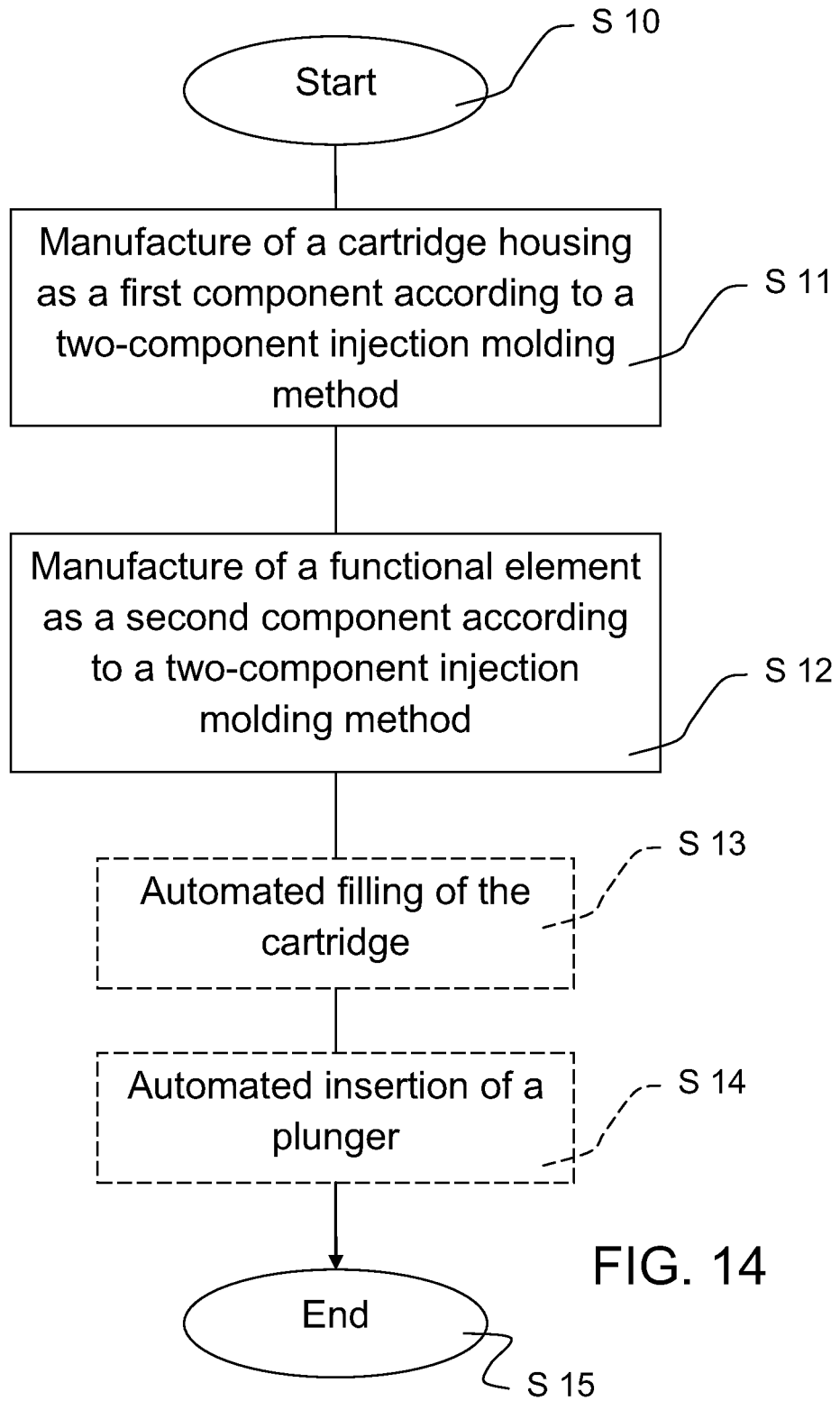
FIG. 14 is another schematic flow chart for a method according to the present invention.

FIG. 14 shows another schematic flow chart for a method according to the present invention. The method according to FIG. 14 extensively corresponds to the method according to FIG. 13. Reference will therefore also made to the preceding description. Contrary to the first method according to FIG. 13, provisions are, however, made according to the other method according to FIG. 14 for the cartridge housing 44 being manufactured first in step S11 as a first component according to a two-component injection molding method. The functional element 15, 46, 51, 54 is subsequently manufactured in step S12 as a second component according to a two-component injection molding method. In case of the functional element 15, this or the plug part 16 fills the cannula duct 24 only partially.

While specific embodiments of the invention have been shown and described in detail to illustrate the application of the principles of the invention, it will be understood that the invention may be embodied otherwise without departing from such principles.

The invention claimed is:

1. A method for manufacturing a cartridge for containing and meterably dispensing a flowable dental material with a reservoir for containing the dental material, the method comprising the steps of:
   connecting the reservoir to a cannula section for dispensing the dental material from the reservoir;
   connecting a separate functional element to the cannula section;
   manufacturing the cartridge together with the functional element according to a multicomponent injection molding method;
   forming the functional element as a detachable closing element;
   positioning the functional element and the cartridge in relation to one another during the manufacture such that the functional element is mounted at least partially in the cannula section;
   providing the functional element with a plug part for closing the cannula section; and
   filling a cannula duct of the cannula section at least partially with the plug part such that the functional element is detachably connected to the cannula section, wherein the cannula duct cannot be reclosed by the functional element after the functional element is removed from the cannula duct.

2. A method in accordance with claim 1, wherein the cartridge is manufactured with a wall thickness reduced in a middle area of the reservoir, the middle area of the reservoir with the reduced wall thickness having a cylindrical shape and/or the middle area of the reservoir extending from a first end of the cartridge with the cannula section and with an end face area to a second end of the cartridge with a cartridge base, wherein the middle area of the reservoir is expanded in the longitudinal direction of the cartridge at a pressure higher than a preset working pressure for dispensing the dental material from the reservoir.

3. A method in accordance with claim 1, wherein the multicomponent injection molding method is designed as a two-component injection molding method, in which the functional element or a cartridge housing is manufactured first in a first step from a first plastic material, and the cartridge housing or the functional element is manufactured in a subsequent, second step from a second plastic material, which is different from the first plastic material, wherein at least one of:
   the functional element is comprised at least one of a thermoplastic elastomer, of thermoplastic silicone, of thermoplastic polyurethane, of liquid silicone and of polyolefin and the cartridge housing is comprised at least one of polyester, of polybutylene terephthalate, of polyethylene terephthalate, of polyolefin, of polypropylene, of polyoxymethylene, of polyamide, of cyclo-olefin copolymers, of cyclo-olefin copolymer mixtures, of polycarbonate, of acrylonitrile-butadiene-styrene and of styrene polymer.

4. A method in accordance with claim 1, wherein the functional element is connected to the cannula section detachably, in a positive-locking and/or non-positive manner, in a frictionally engaged manner, and is arranged in the cannula duct.

5. A method in accordance with claim 1, wherein the cannula duct of the cannula section is completely filled with the plug part and the plug part ends flush at a transition to the reservoir, wherein the closing element has a grip part, which is connected to the plug part and is designed as an information carrier, outside at least one of the cannula section and of the cannula duct.

6. A method in accordance with claim 1, wherein after manufacturing the cartridge with the functional element, the dental material is filled into the reservoir through an opening facing away from the cannula section, in an automated manner, wherein a plunger is inserted into the opening for closing the reservoir, in an automated manner, after filling the reservoir.

7. A method in accordance with claim 1, wherein the functional element is detachably connected to the cannula section via a frictional connection, the frictional connection being defined by at least a portion of the functional element in direct contact with at least a portion of the cannula section.

8. A method for manufacturing a cartridge for containing and meterably dispensing a flowable dental material with a reservoir for containing the dental material, the method comprising the steps of:
   connecting the reservoir to a cannula section for dispensing the dental material from the reservoir;
   connecting a separate functional element to the cannula section;
   manufacturing the cartridge together with the functional element via a molding method;
   forming the functional element as a detachable closing element;
   positioning the functional element and the cartridge in relation to one another during the manufacture such that the functional element is mounted at least partially in the cannula section;
   providing the functional element with a plug part for closing the cannula section; and
   filling a cannula duct of the cannula section at least partially with the plug part such that the cannula duct is detachably connected to the functional element via a frictional engagement between the plug part and at least a portion of the cannula section, wherein the cannula duct cannot be reclosed by the functional element after the functional element is removed from the cannula duct.

9. A method in accordance with claim 8, wherein the cartridge is manufactured with a wall thickness reduced in a middle area of the reservoir, the middle area of the reservoir with the reduced wall thickness having a cylindrical shape and/or the middle area of the reservoir extending from a first end of the cartridge with the cannula section and with an end face area to a second end of the cartridge with a cartridge base, wherein the middle area of the reservoir is expanded in the longitudinal direction of the cartridge at a pressure higher than a preset working pressure for dispensing the dental material from the reservoir.

10. A method in accordance with claim 8, wherein the molding method is designed as a two-component injection molding method, in which the functional element or a cartridge housing is manufactured first in a first step from a first plastic material, and the cartridge housing or the functional element is manufactured in a subsequent, second step from a second plastic material, which is different from the first plastic material, wherein at least one of:
   the functional element is comprised at least one of a thermoplastic elastomer, of thermoplastic silicone, of thermoplastic polyurethane, of liquid silicone and of polyolefin and
   the cartridge housing is comprised at least one of polyester, of polybutylene terephthalate, of polyethylene terephthalate, of polyolefin, of polypropylene, of polyoxymethylene, of polyamide, of cyclo-olefin copolymers, of cyclo-olefin copolymer mixtures, of polycarbonate, of acrylonitrile-butadiene-styrene and of styrene polymer.

11. A method in accordance with claim 8, wherein the functional element is connected to the cannula section detachably, in a positive-locking and/or non-positive manner, in a frictionally engaged manner, and is arranged in the cannula duct.

12. A method in accordance with claim 8, wherein a cannula duct of the cannula section is completely filled with the plug part and the plug part ends flush at the transition to the reservoir, wherein the closing element has a grip part, which is connected to the plug part and is designed as an information carrier, outside at least one of the cannula section and of the cannula duct.

13. A method in accordance with claim 8, wherein after manufacturing the cartridge with the functional element, the dental material is filled into the reservoir through an opening facing away from the cannula section, in an automated manner, wherein a plunger is inserted into the opening for closing the reservoir, in an automated manner, after filling the reservoir.

14. A method for manufacturing a cartridge for containing and meterably dispensing a flowable dental material with a reservoir for containing the dental material, the method comprising the steps of:
   connecting the reservoir to a cannula section for dispensing the dental material from the reservoir;
   connecting a separate functional element to the cannula section;
   manufacturing the cartridge together with the functional element via a molding method;
   forming the functional element as a detachable closing element;
   positioning the functional element and the cartridge in relation to one another during the manufacture such that the functional element is mounted at least partially in the cannula section;
   providing the functional element with a plug part for closing the cannula section; and
   filling a cannula duct of the cannula section at least partially with the plug part such that the cannula section is detachably connected to the functional element via a frictional engagement between the plug part and at least a portion of the cannula section, wherein the functional element is removable from the cannula section by moving the functional element in a direction parallel to a longitudinal axis of the cannula section, wherein the cannula section cannot be reclosed by the functional element after the functional element is removed from the cannula section.

15. A method in accordance with claim 14, wherein the cartridge is manufactured with a wall thickness reduced in a middle area of the reservoir, the middle area of the reservoir with the reduced wall thickness having a cylindrical shape and/or the middle area of the reservoir extending from a first end of the cartridge with the cannula section and with an end face area to a second end of the cartridge with a cartridge base, wherein the middle area of the reservoir is expanded in the longitudinal direction of the cartridge at a pressure higher than a preset working pressure for dispensing the dental material from the reservoir.

16. A method in accordance with claim 14, wherein the molding method is designed as a two-component injection molding method, in which the functional element or a cartridge housing is manufactured first in a first step from a first plastic material, and the cartridge housing or the functional element is manufactured in a subsequent, second step from a second plastic material, which is different from the first plastic material, wherein at least one of:
the functional element is comprised at least one of a thermoplastic elastomer, of thermoplastic silicone, of thermoplastic polyurethane, of liquid silicone and of polyolefin and
the cartridge housing is comprised at least one of polyester, of polybutylene terephthalate, of polyethylene terephthalate, of polyolefin, of polypropylene, of polyoxymethylene, of polyamide, of cyclo-olefin copolymers, of cyclo-olefin copolymer mixtures, of polycarbonate, of acrylonitrile-butadiene-styrene and of styrene polymer.

17. A method in accordance with claim 14, wherein the functional element is arranged in the cannula duct, the cannula duct comprising a cylindrical cannula duct inner surface, the functional element comprising a functional element cylindrical surface, the functional element cylindrical surface being in direct contact with the cylindrical cannula duct inner surface, the cylindrical cannula duct inner surface defining at least a portion of the cannula duct.

18. A method in accordance with claim 14, wherein the cannula duct of the cannula section is completely filled with the plug part and the plug part ends flush at the transition to the reservoir, wherein the closing element has a grip part, which is connected to the plug part and is designed as an information carrier, outside at least one of the cannula section and of the cannula duct.

19. A method in accordance with claim 14, wherein after manufacturing the cartridge with the functional element, the dental material is filled into the reservoir through an opening facing away from the cannula section, in an automated manner, wherein a plunger is inserted into the opening for closing the reservoir, in an automated manner, after filling the reservoir.

20. A method in accordance with claim 14, wherein the cannula section and the functional element are free of threads.

* * * * *